United States Patent

Rueb et al.

Patent Number: 5,106,408
Date of Patent: Apr. 21, 1992

[54] HERBICIDAL THIADIAZABICYCLONONANE DERIVATIVES

[75] Inventors: Lothar Rueb, Speyer; Karl Eicken, Wachenheim; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 561,813

[22] Filed: Aug. 2, 1990

[30] Foreign Application Priority Data

Aug. 19, 1989 [DE] Fed. Rep. of Germany ....... 3927388

[51] Int. Cl.$^5$ .................. C07D 513/04; A01N 43/82
[52] U.S. Cl. ............................................. 71/90; 544/235
[58] Field of Search ............................ 544/235; 71/90

[56] References Cited

U.S. PATENT DOCUMENTS

| | | | |
|---|---|---|---|
| 4,435,208 | 3/1984 | Förster et al. | 71/105 |
| 4,482,736 | 11/1984 | Förster et al. | 560/255 |
| 4,540,827 | 9/1985 | Förster et al. | 568/442 |
| 4,816,063 | 3/1989 | Yamaguchi et al. | 71/90 |
| 4,824,476 | 4/1989 | Pissiotas et al. | 71/95 |
| 4,906,279 | 3/1990 | Yamaguchi et al. | 71/90 |
| 4,913,723 | 4/1990 | Chong | 71/90 |
| 4,925,884 | 5/1990 | Hubner et al. | 523/340 |
| 4,933,001 | 6/1990 | Plath et al. | 71/96 |
| 5,039,331 | 8/1991 | Satow et al. | 71/90 |

FOREIGN PATENT DOCUMENTS

| | | | |
|---|---|---|---|
| 0053321 | 6/1982 | European Pat. Off. | 71/90 |
| 0207894 | 1/1987 | European Pat. Off. | |
| 0238711 | 9/1987 | European Pat. Off. | 71/90 |
| 0319791 | 6/1989 | European Pat. Off. | |
| 3724399 | 2/1989 | Fed. Rep. of Germany | 71/90 |
| 3741273 | 6/1989 | Fed. Rep. of Germany | |

Primary Examiner—Robert Gerstl
Attorney, Agent, or Firm—Keil & Weinkauf

[57] ABSTRACT

Thiadiazabicyclononane derivatives of the formula I

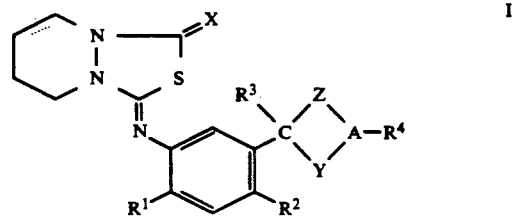

($R^1$=H, F; $R^2$=halogen; $R^3$=H, $C_1$–$C_4$-alkyl; $R^4$=H, $C_1$–$C_8$-alkoxycarbonyl, $C_3$–$C_6$-alkenyloxycarbonyl or $C_3$–$C_5$-alkynyloxycarbonyl, and these 3 groups may additionally bear $C_1$–$C_4$-alkoxy; X, Y, Z=O, S; a=C$_2$–C$_3$-alkylene chain which in addition to $R^4$ may bear up to 3 identical or different radicals $R^5$: OH, COOH, $C_1$–$C_4$-alkyl or $C_1$–$C_6$-alkoxycarbonyl, and the last two radicals may in turn bear up to 5 halogen atoms or one of the following substituents; OH, CN, SH, $C_1$–$C_4$-alkoxy, $C_1$–$C_6$-alkylthio, $C_3$–$C_6$-alkenyloxy, $C_3$–$C_6$-alkenylthio, $C_3$–$C_6$-alkynyloxy, $C_3$–$C_6$-alkynylthio, $C_1$–$C_6$-alkylcarbonyloxy, $C_1$–$C_6$-alkoxycarbonyl, $C_1$–$C_6$-alkoxycarbonyl-$C_1$–$C_4$-alkoxy or $C_1$–$C_6$-alkoxycarbonyl-$C_1$–$C_4$-alkylthio).

These thiadiazabicyclononane derivatives are suitable for use as herbicides.

5 Claims, No Drawings

HERBICIDAL THIADIAZABICYCLONONANE DERIVATIVES

The present invention relates to novel thiadiazabicyclononane derivatives of the general formula I

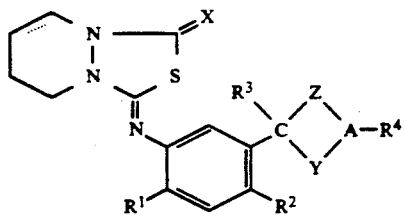

where the dotted bond is a possible additional bond and the substituents have the following meanings:
$R^1$ is hydrogen or fluorine;
$R^2$ is halogen;
$R^3$ is hydrogen or $C_1$-$C_4$-alkyl;
$R^4$ is hydrogen, $C_1$-$C_8$-alkoxycarbonyl, $C_3$-$C_6$-alkenyloxycarbonyl or $C_3$-$C_6$-alkynyloxycarbonyl, it being possible for each of these 3 groups to additionally carry a $C_1$-$C_4$-alkoxy radical;
X, Y and Z are oxygen or sulfur;
A is a $C_2$-$C_3$-alkylene chain which, in addition to $R^4$, may carry up to three identical or different radicals $R^5$: hydroxyl, carboxyl, $C_1$-$C_4$-alkyl or $C_1$-$C_6$-alkoxycarbonyl, it being possible for the two lastmentioned radicals themselves to carry up to 5 halogen atoms and/or one of the following substituents: hydroxyl, cyano, mercapto, $C_1$-$C_4$-alkoxy, $C_1$-$C_6$-thio, $C_3$-$C_6$-alkenyloxy, $C_3$-$C_6$-alkenylthio, $C_3$-$C_6$-alkynyloxy, $C_3$-$C_6$-alkynylthio, $C_1$-$C_6$-alkoxycarbonyl-$C_1$-$C_4$-alkoxy or $C_1$-$C_6$-alkoxycarbonyl-$C_1$-$C_4$-alkylthio.

The present invention furthermore relates to processes for the preparation of these compounds, and to the use thereof as herbicides.

Herbicidal acetals and thioacetals of benzaldehyde whose phenyl ring is substituted in the metaposition to the acetal group by a tetrahydrophthalimide radical and which, in addition, carries comparable substituents $R^1$ and $R^2$ have been disclosed in EP-A-207,894, EP-A-0,319,791, DE-A-3,741,273 and DE-A-....... (P 3916292.3).

However, compounds which exhibit a good herbicidal action at low application rates are desirable.

It was therefore an object of the present invention to provide novel substances having an improved herbicidal action.

We have found that this object is achieved by the thiadiazabicyclononane derivatives I defined at the outset.

In addition, processes for the preparation of the compounds I, the use of these compounds as herbicides and herbicides containing these compounds have been found.

The compounds I are obtained, for example, by acetalating nitrobenzene of the general formula II in a conventional manner (Ferri, Reaktionen der org. Synthese; G. Thieme Verlag Stuttgart, pages 27ff.) using a compound IIIa in an inert organic solvent in the presence of an acid at from 0 to 180° C. preferably from 25 to 150° C., subsequently reducing the resultant acetal or thioacetal IV to give the aniline derivative V, and reacting V with thiophosgene to give the isothiocyanate VI, subjecting VI to an addition reaction with a cyclic hydrazine of the formula VII, and finally cyclizing the product.

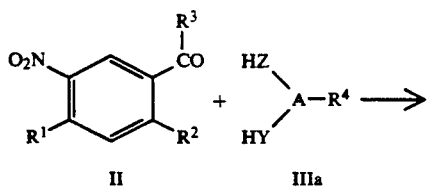

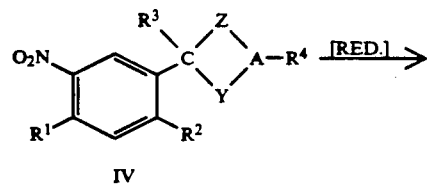

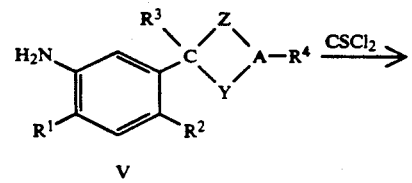

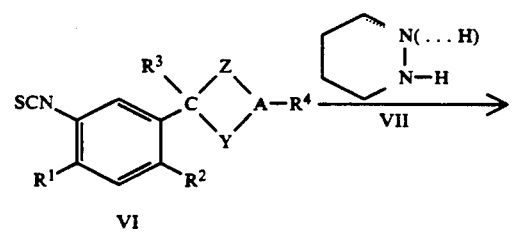

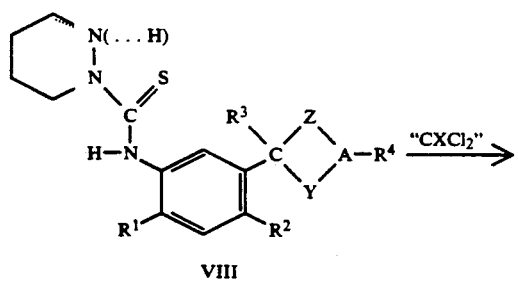

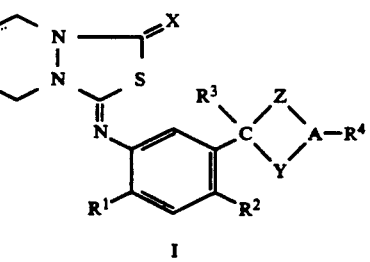

The acetalation of II using IIIa is preferably carried out in an aprotic organic solvent, such as toluene or xylene, in particular toluene, in the presence of an acid, such as p-toluenesulfonic acid as catalyst.

The reduction of the resultant acetal IV to give the aniline derivative V is carried out by generally conventional methods (Houben-Weyl, Vol. 4/1c, pages 507ff. and Vol. 4/1d, pages 470ff.), for example in the presence of inorganic reducing agents such as iron and tin (II) salts in aprotic polar solvents or in the presence of hydrogen on metal catalysts, such as platinum, palladium or Raney nickel, in aprotic polar solvents.

The formation of the isothiocyanates VI is carried out in a conventional manner at from 0 to 100° C., preferably at from 20 to 50° C., in a two-phase system, for example methylene chloride/water, or in an inert solvent, such as toluene, with addition of an organic base, eg. tert.-amines such as triethylamine.

The isothiocyanates VI are reacted with the compounds of the formula VII in aprotic polar solvents, such as tetrahydrofuran, at from 0 to 100° C., preferably at from 20 to 50° C. The cyclization to form the compounds of the general formula I is carried out at from 0 to 100° C., preferably at from 20 to 70° C., in a solvent, such as methylene chloride, with addition of a base, such as pyridine, by adding a phosgenating agent such as phosgene, thiophosgene or trichloromethyl chloroformate.

The process is generally carried out at atmospheric pressure or under the autogenous pressure of the particular solvent.

If $R^4$ is hydrogen and A is an ethylene or propylene chain, which may carry from 1 to 3 $C_1$-$C_3$-alkyl groups, preferably methyl or ethyl, these thiadiazabicyclononane derivatives I can be transacetalated in a conventional manner to give further compounds I according to the invention.

In general, the molar ratios between starting compounds in the individual stages are from 1:1 to 1:2.

From equimolar amounts up to an approximately 5-fold excess, preferably a 3-fold excess, based on the amount of compound IV, of reducing agent are recommended for the reduction of the nitro compound IV to give the aniline derivative V.

The concentration of the starting materials in the solvent is generally from 0.05 to 5 mol/l, preferably from 0.1 to 2.5 mol/l.

The starting materials required are generally known or can be prepared by known methods.

As far as the use of the compounds I according to the invention as herbicides is concerned, the following radicals are preferred as substituents:

$R^1$ is hydrogen or fluorine, preferably hydrogen;
$R^2$ is halogen, such as fluorine, chlorine, bromine or iodine, preferably fluorine or chlorine;
$R^3$ is hydrogen or alkyl, such as methyl, ethyl, n-propyl, isopropyl, n-butyl, i-butyl, sec.-butyl or tert.-butyl, preferably hydrogen, methyl or ethyl;
$R^4$ is hydrogen, alkoxycarbonyl, such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl, pentoxycarbonyl, 1-methylbutoxycarbonyl, 2-methylbutoxycarbonyl, 3-methylbutoxycarbonyl, 1,2-dimethylpropyloxycarbonyl, 1,1-dimethylpropyloxycarbonyl, 2,2-dimethylpropyloxycarbonyl, 1-ethylpropyloxycarbonyl, n-hexyloxycarbonyl, 1-methylpentyloxycarbonyl, 2-methylpentyloxycarbonyl, 3methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropyloxycarbonyl, 1,2,2-trimethylpropyloxycarbonyl, 1-ethylbutoxycarbonyl, 2-ethylbutoxycarbonyl or 1-ethyl-2-methylpropyloxycarbonyl; alkenyloxycarbonyl, such as 2-propenyloxycarbonyl, 2-butenyloxycarbonyl, 3-butenyloxycarbonyl, 1-methyl-2-propenyloxycarbonyl, 2-methyl-2-propenyloxycarbonyl, 2-pentenyloxycarbonyl, 3-pentenyloxycarbonyl, 4-pentenyloxycarbonyl, 1-methyl-2-butenyloxycarbonyl, 2-methyl-2-butenyloxycarbonyl, 3-methyl-2-butenyloxycarbonyl, 1-methyl-3-butenyloxycarbonyl, 2-methyl-3-butenyloxycarbonyl, 3-methyl-3-butenyloxycarbonyl, 1,1-dimethyl-2-propenyloxycarbonyl, 1,2-dimethyl-2-propenyloxycarbonyl, 1-ethyl-2-propenyloxycarbonyl, 2-hexenyloxycarbonyl, 3-hexenyloxycarbonyl, 4-hexenyloxycarbonyl, 5-hexenyloxycarbonyl, 1-methyl-2-pentenyloxycarbonyl, 2-methyl-2-pentenyloxycarbonyl, 3-methyl-2-pentenyloxycarbonyl, 4-methyl-2-pentenyloxycarbonyl, 1-methyl-3-pentenyloxycarbonyl, 2-methyl-3-pentenyloxycarbonyl, 3-methyl-3-pentenyloxycarbonyl, 4-methyl-3-pentenyloxycarbonyl, 1-methyl-4-pentenyloxycarbonyl, 2-methyl-4-pentenyloxycarbonyl, 3-methyl-4-pentenyloxycarbonyl, 4-methyl-4-pentenyloxycarbonyl, 1,1-dimethyl-2-butenyloxycarbonyl, 1,1-dimethyl-3-butenyloxycarbonyl, 1,2-dimethyl-2-butenyloxycarbonyl, 1,2-dimethyl-3-butenyloxycarbonyl, 1,3-dimethyl-2-butenyloxycarbonyl, 1,3-dimethyl-3-butenyloxycarbonyl, 2,2-dimethyl-3butenyloxycarbonyl, 2,3-dimethyl-2-butenyloxycarbonyl, 2,3-dimethyl-3-butenyloxycarbonyl, 1-ethyl-2-butenyloxycarbonyl, 1-ethyl-3-butenyloxycarbonyl, 2-ethyl-2-butenyloxycarbonyl, 2-ethyl-3-butenyloxycarbonyl, 1,1,2-trimethyl-2-propenyloxycarbonyl, 1-ethyl-1-methyl-2-propenyloxycarbonyl or 1-ethyl-2-methyl-2-propenyloxycarbonyl; alkynyloxycarbonyl, such as 2-propenyloxycarbonyl, 2-butenyloxycarbonyl, 3-butenyloxycarbonyl, 1-methyl-2-propenyloxycarbonyl, 2-pentenyloxycarbonyl, 3-pentenyloxycarbonyl, 4-pentenyloxycarbonyl, 1-methyl-3-butenyloxycarbonyl, 2-methyl-3-butenyloxycarbonyl 1-methyl-2-butenyloxycarbonyl, 1,1-dimethyl-2-propenyloxycarbonyl, 1-ethyl-2-propenyloxycarbonyl, 2-hexenyloxycarbonyl, 3-hexenyloxycarbonyl, 4-hexenyloxycarbonyl, 5-hexenyloxycarbonyl, 1-methyl-2-pentenyloxycarbonyl, 1-methyl-3-pentenyloxycarbonyl, 1-methyl-4-pentenyloxycarbonyl, 2-methyl-3-pentenyloxycarbonyl, 2-methyl-4-pentenyloxycarbonyl, 3-methyl-4-pentenyloxycarbonyl, 4-methyl-2-pentenyloxycarbonyl, 1,1-dimethyl-2-butenyloxycarbonyl, 1,1-dimethyl-3-butenyloxycarbonyl, 1,2-dimethyl-3-butenyloxycarbonyl, 2,2-dimethyl-3-butenyloxycarbonyl, 1-ethyl-2-butenyloxycarbonyl, 1-ethyl-3-butenyloxycarbonyl, 2-ethyl-3-butenyloxycarbonyl or 1-ethyl-1-methyl-2-propenyloxycarbonyl;

it being possible for these groups to additionally carry an alkoxy radical, such as methoxy, ethoxy, propoxy, 1-methylethoxy, butoxy, 1-methylpropoxy, 2-methylpropoxy or 1,1-dimethylethoxy, preferably methoxy or ethoxy;

X and Y are oxygen or sulfur, preferably oxygen;
A is alkylene, such as 1,2-ethylene or 1,3-propylene, which may carry from one to three of the following radicals: hydroxyl; carboxyl; alkyl or alkoxycarbonyl, as mentioned in general and preferred terms in the case of $R^3$ and $R^4$ respectively, it being possible for the two last-mentioned radicals to themselves carry from one to five halogen atoms as mentioned in the case of $R^2$ or to carry one of the following radicals:cyano; mercapto; alkoxy as mentioned in the case of R⁴; alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-penenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy,1,1,2-trimethyl-2-propenyloxy, 1-ethyl-1-methyl-2-propenyloxy or 1-ethyl-2-methyl-2-propenyloxy; alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy or 1-ethyl-1-methyl-2-propynyloxy; alkylcarbonyloxy, such as methylcarbonyloxy, ethylcarbonyloxy, propylcarbonyloxy, 1-methylethylcarbonyloxy, butylcarbonyloxy, 1-methylpropylcarbonyloxy, 2-methylpropylcarbonyloxy, 1,1-dimethylethylcarbonyloxy, pentylcarbonyloxy, 1-methylbutylcarbonyloxy, 2-methylbutylcarbonyloxy, 3-methylbutylcarbonyloxy, 1,2-dimethylpropylcarbonyloxy, 1,1-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentylcarbonyloxy, 4-methylpentylcarbonyloxy, 1,2-dimethylbutylcarbonyloxy, 1,3-dimethylbutylcarbonyloxy, 2,3-dimethylbutylcarbonyloxy, 1,1-dimethylbutylcarbonyloxy, 2,2-dimethylbutylcarbonyloxy, 3,3-dimethylbutylcarbonyloxy, 1,1,2-trimethylpropylcarbonyloxy, 1,2,2-trimethylpropylcarbonyloxy, 1-ethylbutylcarbonyloxy, 2-ethylbutylcarbonyloxy, or 1-ethyl-2-methylpropylcarbonyloxy; alkylthio, such as methylthio, ethylthio, 1-methylethylthio, butylthio, 1-methylpropylthio, 2-methylpropylthio or 1,1-dimethylethylthio; alkenylthio, such as 2-propenylthio, 2-butenylthio, 3-butenylthio, 1-methyl-2-propenylthio, 2-methyl-2-propenylthio, 2-pentenylthio, 3-pentenylthio, 4-pentenylthio, 1-methyl-2-butenylthio, 2-methyl-2-butenylthio, 3-methyl-2-butenylthio, 1-methyl-3-butenylthio, 2-methyl-3-butenylthio, 3-methyl-3-butenylthio, 1,1-dimethyl-2-propenylthio, 1,2-dimethyl-2-propenylthio, 1-ethyl-2-propenylthio, 2-hexenylthio, 3-hexenylthio, 4-hexenylthio, 5-hexenylthio, 1-methyl-2-pentenylthio, 2-methyl-2-pentenylthio, 3-methyl-2-pentenylthio, 4-methyl-2-pentenylthio, 1-methyl-3-pentenylthio, 2-methyl-3-pentenylthio, 3-methyl-3-pentenylthio, 4-methyl-3-pentenylthio, 1-methyl-4-pentenylthio, 2-methyl-4-pentenylthio, 3-methyl-4-pentenylthio, 4-methyl-4-pentenylthio, 1,1-dimethyl-2-butenylthio, 1,1-dimethyl-3-butenylthio, 1,2-dimethyl-2-butenylthio, 1,2-dimethyl-3-butenylthio, 1,3-dimethyl-1-butenylthio, 1,3-dimethyl-2-butenylthio, 1,3-dimethyl-3-butenylthio, 2,2-dimethyl-3-butenylthio, 2,3-dimethyl-2-butenylthio, 2,3-dimethyl-3-butenylthio, 1-ethyl-2-butenylthio, 1-ethyl-3-butenylthio, 2-ethyl-2-butenylthio,2-ethyl-3-butenylthio, 1,1,2-trimethyl-2-propenylthio, 1-ethyl-1-methyl-2-propenylthio or 1-ethyl-2-methyl-2-propenylthio; alkynylthio, such as 2-propynylthio, 2-butynylthio, 3-butynylthio, 1-methyl-2-propynylthio, 2-pentynylthio, 3-pentynylthio, 4-pentynylthio, 1-methyl-3-butynylthio, 2-methyl-3-butynylthio, 1-methyl-2-butynylthio, 1,1-dimethyl-2-propynylthio, 1-ethyl-2-propynylthio,2-hexynylthio, 3-hexynylthio, 4-hexynylthio, 5-hexynylthio, 1-methyl-2-pentynylthio, 1-methyl-3-pentynylthio, 1-methyl-4-pentynylthio, 2-methyl-3-pentynylthio, 2-methyl-4-pentynylthio, 3-methyl-4-pentynylthio, 4-methyl-2-pentynylthio, 1,1-dimethyl-2-butynylthio, 1,1-dimethyl-3-butynylthio, 1,2-dimethyl-3-butynylthio,2,2-dimethyl-3-butynylthio, 2-ethyl-3-butynylthio or 1-ethyl-1-methyl-2-propynylthio or alkoxycarbonyl as mentioned in the case of R⁴, which may be bonded directly or via one of the abovementioned alkoxy or alkylthio groups.

Particularly preferred compounds are those of the formulae Ia to If (m=0 or 1).

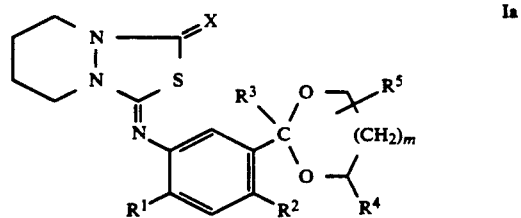

Ia

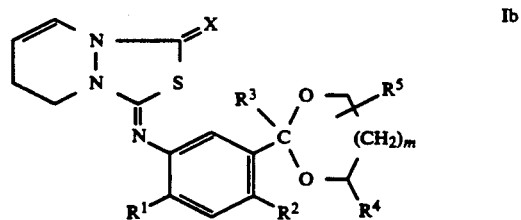

Ib

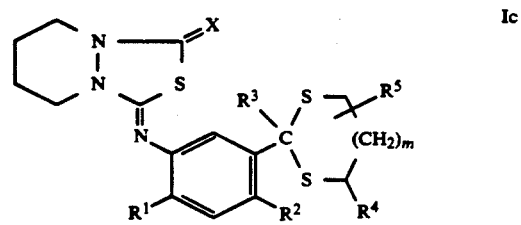

Ic

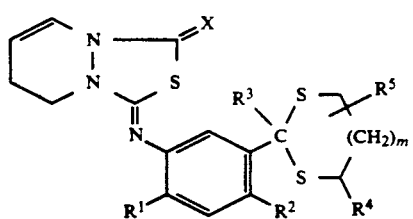

Id

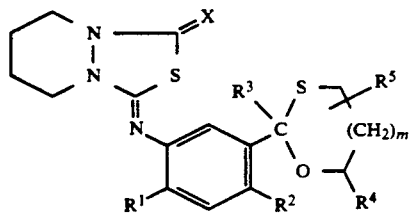

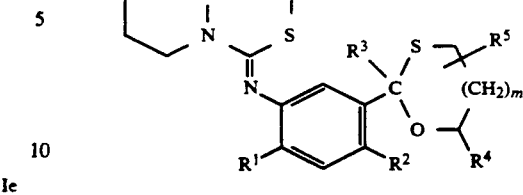

If

Table 1 lists examples of possible substituents of particularly preferred compounds Ia to Id, and Table 2 possible substituents of particularly preferred compounds Ie and If.

TABLE 1

| X | R¹ | R² | R³ | m | R⁵ | R⁴ |
|---|----|----|----|---|----|----|
| S | H | F | H | 0 | H | H |
| O | H | F | H | 0 | H | H |
| S | F | F | H | 0 | H | H |
| O | F | F | H | 0 | H | H |
| S | H | Cl | H | 0 | H | H |
| O | H | Cl | H | 0 | H | H |
| S | F | Cl | H | 0 | H | H |
| O | F | Cl | H | 0 | H | H |
| S | H | F | CH₃ | 0 | H | H |
| O | H | F | CH₃ | 0 | H | H |
| S | F | F | CH₃ | 0 | H | H |
| O | F | F | CH₃ | 0 | H | H |
| S | H | Cl | CH₃ | 0 | H | H |
| O | H | Cl | CH₃ | 0 | H | H |
| S | F | Cl | CH₃ | 0 | H | H |
| O | F | Cl | CH₃ | 0 | H | H |
| S | H | F | H | 0 | 4-CH₃ | H |
| O | H | F | H | 0 | 4-CH₃ | H |
| S | F | F | H | 0 | 4-CH₃ | H |
| O | F | F | H | 0 | 4-CH₃ | H |
| S | H | Cl | H | 0 | 4-CH₃ | H |
| O | H | Cl | H | 0 | 4-CH₃ | H |
| S | F | Cl | H | 0 | 4-CH₃ | H |
| O | F | Cl | H | 0 | 4-CH₃ | H |
| S | H | F | CH₃ | 0 | 4-CH₃ | H |
| O | H | F | CH₃ | 0 | 4-CH₃ | H |
| S | F | F | CH₃ | 0 | 4-CH₃ | H |
| O | F | F | CH₃ | 0 | 4-CH₃ | H |
| S | H | Cl | CH₃ | 0 | 4-CH₃ | H |
| O | H | Cl | CH₃ | 0 | 4-CH₃ | H |
| S | F | Cl | CH₃ | 0 | 4-CH₃ | H |
| O | F | Cl | CH₃ | 0 | 4-CH₃ | H |
| S | H | F | H | 0 | 4,5-Di-CH₃ | H |
| O | H | F | H | 0 | 4,5-Di-CH₃ | H |
| S | F | F | H | 0 | 4,5-Di-CH₃ | H |
| O | F | F | H | 0 | 4,5-Di-CH₃ | H |
| S | H | Cl | H | 0 | 4,5-Di-CH₃ | H |
| O | H | Cl | H | 0 | 4,5-Di-CH₃ | H |
| S | F | Cl | H | 0 | 4,5-Di-CH₃ | H |
| O | F | Cl | H | 0 | 4,5-Di-CH₃ | H |
| S | H | F | CH₃ | 0 | 4,5-Di-CH₃ | H |
| O | H | F | CH₃ | 0 | 4,5-Di-CH₃ | H |
| S | F | F | CH₃ | 0 | 4,5-Di-CH₃ | H |
| O | F | F | CH₃ | 0 | 4,5-Di-CH₃ | H |
| S | H | Cl | CH₃ | 0 | 4,5-Di-CH₃ | H |
| O | H | Cl | CH₃ | 0 | 4,5-Di-CH₃ | H |
| S | F | Cl | CH₃ | 0 | 4,5-Di-CH₃ | H |
| O | F | Cl | CH₃ | 0 | 4,5-Di-CH₃ | H |
| S | H | F | H | 0 | 4-CH₂CH₃ | H |
| O | H | F | H | 0 | 4-CH₂CH₃ | H |
| S | F | F | H | 0 | 4-CH₂CH₃ | H |
| O | F | F | H | 0 | 4-CH₂CH₃ | H |
| S | H | Cl | H | 0 | 4-CH₂CH₃ | H |
| O | H | Cl | H | 0 | 4-CH₂CH₃ | H |
| S | F | Cl | H | 0 | 4-CH₂CH₃ | H |
| O | F | Cl | H | 0 | 4-CH₂CH₃ | H |
| S | H | F | CH₃ | 0 | 4-CH₂CH₃ | H |

TABLE 1-continued

| X | R¹ | R² | R³ | m | R⁵ | R⁴ |
|---|----|----|----|---|----|----|
| O | H | F | CH₃ | 0 | 4-CH₂CH₃ | H |
| S | F | F | CH₃ | 0 | 4-CH₂CH₃ | H |
| O | F | F | CH₃ | 0 | 4-CH₂CH₃ | H |
| S | H | Cl | CH₃ | 0 | 4-CH₂CH₃ | H |
| O | H | Cl | CH₃ | 0 | 4-CH₂CH₃ | H |
| S | F | Cl | CH₃ | 0 | 4-CH₂CH₃ | H |
| O | F | Cl | CH₃ | 0 | 4-CH₂CH₃ | H |
| S | H | F | H | 0 | 4-CH₂Cl | H |
| O | H | F | H | 0 | 4-CH₂Cl | H |
| S | F | F | H | 0 | 4-CH₂Cl | H |
| O | F | F | H | 0 | 4-CH₂Cl | H |
| S | H | Cl | H | 0 | 4-CH₂Cl | H |
| O | H | Cl | H | 0 | 4-CH₂Cl | H |
| S | F | Cl | H | 0 | 4-CH₂Cl | H |
| O | F | Cl | H | 0 | 4-CH₂Cl | H |
| S | H | F | CH₃ | 0 | 4-CH₂Cl | H |
| O | H | F | CH₃ | 0 | 4-CH₂Cl | H |
| S | F | F | CH₃ | 0 | 4-CH₂Cl | H |
| O | F | F | CH₃ | 0 | 4-CH₂Cl | H |
| S | H | Cl | CH₃ | 0 | 4-CH₂Cl | H |
| O | H | Cl | CH₃ | 0 | 4-CH₂Cl | H |
| S | F | Cl | CH₃ | 0 | 4-CH₂Cl | H |
| O | F | Cl | CH₃ | 0 | 4-CH₂Cl | H |
| S | H | F | H | 0 | 4-CH₂OH | H |
| O | H | F | H | 0 | 4-CH₂OH | H |
| S | F | F | H | 0 | 4-CH₂OH | H |
| O | F | F | H | 0 | 4-CH₂OH | H |
| S | H | Cl | H | 0 | 4-CH₂OH | H |
| O | H | Cl | H | 0 | 4-CH₂OH | H |
| S | F | Cl | H | 0 | 4-CH₂OH | H |
| O | F | Cl | H | 0 | 4-CH₂OH | H |
| S | H | F | CH₃ | 0 | 4-CH₂OH | H |
| O | H | F | CH₃ | 0 | 4-CH₂OH | H |
| S | F | F | CH₃ | 0 | 4-CH₂OH | H |
| O | F | F | CH₃ | 0 | 4-CH₂OH | H |
| S | H | Cl | CH₃ | 0 | 4-CH₂OH | H |
| O | H | Cl | CH₃ | 0 | 4-CH₂OH | H |
| S | F | Cl | CH₃ | 0 | 4-CH₂OH | H |
| O | F | Cl | CH₃ | 0 | 4-CH₂OH | H |
| S | H | F | H | 0 | 4-CH₂OCH₃ | H |
| O | H | F | H | 0 | 4-CH₂OCH₃ | H |
| S | F | F | H | 0 | 4-CH₂OCH₃ | H |
| O | F | F | H | 0 | 4-CH₂OCH₃ | H |
| S | H | Cl | H | 0 | 4-CH₂OCH₃ | H |
| O | H | Cl | H | 0 | 4-CH₂OCH₃ | H |
| S | F | Cl | H | 0 | 4-CH₂OCH₃ | H |
| O | F | Cl | H | 0 | 4-CH₂OCH₃ | H |
| S | H | F | CH₃ | 0 | 4-CH₂OCH₃ | H |
| O | H | F | CH₃ | 0 | 4-CH₂OCH₃ | H |
| S | F | F | CH₃ | 0 | 4-CH₂OCH₃ | H |
| O | F | F | CH₃ | 0 | 4-CH₂OCH₃ | H |
| S | H | Cl | CH₃ | 0 | 4-CH₂OCH₃ | H |
| O | H | Cl | CH₃ | 0 | 4-CH₂OCH₃ | H |
| S | F | Cl | CH₃ | 0 | 4-CH₂OCH₃ | H |
| O | F | Cl | CH₃ | 0 | 4-CH₂OCH₃ | H |
| S | H | F | H | 0 | 4-CH₂OCH₂CH=CH₂ | H |
| O | H | F | H | 0 | 4-CH₂OCH₂CH=CH₂ | H |
| S | F | F | H | 0 | 4-CH₂OCH₂CH=CH₂ | H |
| O | F | F | H | 0 | 4-CH₂OCH₂CH=CH₂ | H |
| S | H | Cl | H | 0 | 4-CH₂OCH₂CH=CH₂ | H |
| O | H | Cl | H | 0 | 4-CH₂OCH₂CH=CH₂ | H |
| S | F | Cl | H | 0 | 4-CH₂OCH₂CH=CH₂ | H |
| O | F | Cl | H | 0 | 4-CH₂OCH₂CH=CH₂ | H |
| S | H | F | CH₃ | 0 | 4-CH₂OCH₂CH=CH₂ | H |
| O | H | F | CH₃ | 0 | 4-CH₂OCH₂CH=CH₂ | H |
| S | F | F | CH₃ | 0 | 4-CH₂OCH₂CH=CH₂ | H |
| O | F | F | CH₃ | 0 | 4-CH₂OCH₂CH=CH₂ | H |
| S | H | Cl | CH₃ | 0 | 4-CH₂OCH₂CH=CH₂ | H |
| O | H | Cl | CH₃ | 0 | 4-CH₂OCH₂CH=CH₂ | H |
| S | F | Cl | CH₃ | 0 | 4-CH₂OCH₂CH=CH₂ | H |
| O | F | Cl | CH₃ | 0 | 4-CH₂OCH₂CH=CH₂ | H |
| S | H | F | H | 0 | 4-CH₂OCH₂C≡CH | H |
| O | H | F | H | 0 | 4-CH₂OCH₂C≡CH | H |
| S | F | F | H | 0 | 4-CH₂OCH₂C≡CH | H |
| O | F | F | H | 0 | 4-CH₂OCH₂C≡CH | H |
| S | H | Cl | H | 0 | 4-CH₂OCH₂C≡CH | H |
| O | H | Cl | H | 0 | 4-CH₂OCH₂C≡CH | H |
| S | F | Cl | H | 0 | 4-CH₂OCH₂C≡CH | H |
| O | F | Cl | H | 0 | 4-CH₂OCH₂C≡CH | H |
| S | H | F | CH₃ | 0 | 4-CH₂OCH₂C≡CH | H |
| O | H | F | CH₃ | 0 | 4-CH₂OCH₂C≡CH | H |

TABLE 1-continued

| X | R$^1$ | R$^2$ | R$^3$ | m | R$^5$ | R$^4$ |
|---|---|---|---|---|---|---|
| S | F | F | CH$_3$ | 0 | 4-CH$_2$OCH$_2$C≡CH | H |
| O | F | F | CH$_3$ | 0 | 4-CH$_2$OCH$_2$C≡CH | H |
| S | H | Cl | CH$_3$ | 0 | 4-CH$_2$OCH$_2$C≡CH | H |
| O | H | Cl | CH$_3$ | 0 | 4-CH$_2$OCH$_2$C≡CH | H |
| S | F | Cl | CH$_3$ | 0 | 4-CH$_2$OCH$_2$C≡CH | H |
| O | F | Cl | CH$_3$ | 0 | 4-CH$_2$OCH$_2$C≡CH | H |
| S | H | F | H | 0 | 4-CH$_2$OCOCH$_3$ | H |
| O | H | F | H | 0 | 4-CH$_2$OCOCH$_3$ | H |
| S | F | F | H | 0 | 4-CH$_2$OCOCH$_3$ | H |
| O | F | F | H | 0 | 4-CH$_2$OCOCH$_3$ | H |
| S | H | Cl | H | 0 | 4-CH$_2$OCOCH$_3$ | H |
| O | H | Cl | H | 0 | 4-CH$_2$OCOCH$_3$ | H |
| S | F | Cl | H | 0 | 4-CH$_2$OCOCH$_3$ | H |
| O | F | Cl | H | 0 | 4-CH$_2$OCOCH$_3$ | H |
| S | H | F | CH$_3$ | 0 | 4-CH$_2$OCOCH$_3$ | H |
| O | H | F | CH$_3$ | 0 | 4-CH$_2$OCOCH$_3$ | H |
| S | F | F | CH$_3$ | 0 | 4-CH$_2$OCOCH$_3$ | H |
| O | F | F | CH$_3$ | 0 | 4-CH$_2$OCOCH$_3$ | H |
| S | H | Cl | CH$_3$ | 0 | 4-CH$_2$OCOCH$_3$ | H |
| O | H | Cl | CH$_3$ | 0 | 4-CH$_2$OCOCH$_3$ | H |
| S | F | Cl | CH$_3$ | 0 | 4-CH$_2$OCOCH$_3$ | H |
| O | F | Cl | CH$_3$ | 0 | 4-CH$_2$OCOCH$_3$ | H |
| S | H | F | H | 0 | 4-CH$_2$OCH$_2$CO$_2$CH$_3$ | H |
| O | H | F | H | 0 | 4-CH$_2$OCH$_2$CO$_2$CH$_3$ | H |
| S | F | F | H | 0 | 4-CH$_2$OCH$_2$CO$_2$CH$_3$ | H |
| O | F | F | H | 0 | 4-CH$_2$OCH$_2$CO$_2$CH$_3$ | H |
| S | H | Cl | H | 0 | 4-CH$_2$OCH$_2$CO$_2$CH$_3$ | H |
| O | H | Cl | H | 0 | 4-CH$_2$OCH$_2$CO$_2$CH$_3$ | H |
| S | F | Cl | H | 0 | 4-CH$_2$OCH$_2$CO$_2$CH$_3$ | H |
| O | F | Cl | H | 0 | 4-CH$_2$OCH$_2$CO$_2$CH$_3$ | H |
| S | H | F | CH$_3$ | 0 | 4-CH$_2$OCH$_2$CO$_2$CH$_3$ | H |
| O | H | F | CH$_3$ | 0 | 4-CH$_2$OCH$_2$CO$_2$CH$_3$ | H |
| S | F | F | CH$_3$ | 0 | 4-CH$_2$OCH$_2$CO$_2$CH$_3$ | H |
| O | F | F | CH$_3$ | 0 | 4-CH$_2$OCH$_2$CO$_2$CH$_3$ | H |
| S | H | Cl | CH$_3$ | 0 | 4-CH$_2$OCH$_2$CO$_2$CH$_3$ | H |
| O | H | Cl | CH$_3$ | 0 | 4-CH$_2$OCH$_2$CO$_2$CH$_3$ | H |
| S | F | Cl | CH$_3$ | 0 | 4-CH$_2$OCH$_2$CO$_2$CH$_3$ | H |
| O | F | Cl | CH$_3$ | 0 | 4-CH$_2$OCH$_2$CO$_2$CH$_3$ | H |
| S | H | F | H | 0 | 4-CH$_2$CO$_2$CH$_3$ | H |
| O | H | F | H | 0 | 4-CH$_2$CO$_2$CH$_3$ | H |
| S | F | F | H | 0 | 4-CH$_2$CO$_2$CH$_3$ | H |
| O | F | F | H | 0 | 4-CH$_2$CO$_2$CH$_3$ | H |
| S | H | Cl | H | 0 | 4-CH$_2$CO$_2$CH$_3$ | H |
| O | H | Cl | H | 0 | 4-CH$_2$CO$_2$CH$_3$ | H |
| S | F | Cl | H | 0 | 4-CH$_2$CO$_2$CH$_3$ | H |
| O | F | Cl | H | 0 | 4-CH$_2$CO$_2$CH$_3$ | H |
| S | H | F | CH$_3$ | 0 | 4-CH$_2$CO$_2$CH$_3$ | H |
| O | H | F | CH$_3$ | 0 | 4-CH$_2$CO$_2$CH$_3$ | H |
| S | F | F | CH$_3$ | 0 | 4-CH$_2$CO$_2$CH$_3$ | H |
| O | F | F | CH$_3$ | 0 | 4-CH$_2$CO$_2$CH$_3$ | H |
| S | H | Cl | CH$_3$ | 0 | 4-CH$_2$CO$_2$CH$_3$ | H |
| O | H | Cl | CH$_3$ | 0 | 4-CH$_2$CO$_2$CH$_3$ | H |
| S | F | Cl | CH$_3$ | 0 | 4-CH$_2$CO$_2$CH$_3$ | H |
| O | F | Cl | CH$_3$ | 0 | 4-CH$_2$CO$_2$CH$_3$ | H |
| S | H | F | H | 0 | 4-CH$_2$SH | H |
| O | H | F | H | 0 | 4-CH$_2$SH | H |
| S | F | F | H | 0 | 4-CH$_2$SH | H |
| O | F | F | H | 0 | 4-CH$_2$SH | H |
| S | H | Cl | H | 0 | 4-CH$_2$SH | H |
| O | H | Cl | H | 0 | 4-CH$_2$SH | H |
| S | F | Cl | H | 0 | 4-CH$_2$SH | H |
| O | F | Cl | H | 0 | 4-CH$_2$SH | H |
| S | H | F | CH$_3$ | 0 | 4-CH$_2$SH | H |
| O | H | F | CH$_3$ | 0 | 4-CH$_2$SH | H |
| S | F | F | CH$_3$ | 0 | 4-CH$_2$SH | H |
| O | F | F | CH$_3$ | 0 | 4-CH$_2$SH | H |
| S | H | Cl | CH$_3$ | 0 | 4-CH$_2$SH | H |
| O | H | Cl | CH$_3$ | 0 | 4-CH$_2$SH | H |
| S | F | Cl | CH$_3$ | 0 | 4-CH$_2$SH | H |
| O | F | Cl | CH$_3$ | 0 | 4-CH$_2$SH | H |
| S | H | F | H | 0 | 4-CH$_2$SCH$_2$CH$_3$ | H |
| O | H | F | H | 0 | 4-CH$_2$SCH$_2$CH$_3$ | H |
| S | F | F | H | 0 | 4-CH$_2$SCH$_2$CH$_3$ | H |
| O | F | F | H | 0 | 4-CH$_2$SCH$_2$CH$_3$ | H |
| S | H | Cl | H | 0 | 4-CH$_2$SCH$_2$CH$_3$ | H |
| O | H | Cl | H | 0 | 4-CH$_2$SCH$_2$CH$_3$ | H |
| S | F | Cl | H | 0 | 4-CH$_2$SCH$_2$CH$_3$ | H |
| O | F | Cl | H | 0 | 4-CH$_2$SCH$_2$CH$_3$ | H |
| S | H | F | CH$_3$ | 0 | 4-CH$_2$SCH$_2$CH$_3$ | H |
| O | H | F | CH$_3$ | 0 | 4-CH$_2$SCH$_2$CH$_3$ | H |
| S | F | F | CH$_3$ | 0 | 4-CH$_2$SCH$_2$CH$_3$ | H |

TABLE 1-continued

| X | R¹ | R² | R³ | m | R⁵ | R⁴ |
|---|---|---|---|---|---|---|
| O | F | F | CH₃ | 0 | 4-CH₂SCH₂CH₃ | H |
| S | H | Cl | CH₃ | 0 | 4-CH₂SCH₂CH₃ | H |
| O | H | Cl | CH₃ | 0 | 4-CH₂SCH₂CH₃ | H |
| S | F | Cl | CH₃ | 0 | 4-CH₂SCH₂CH₃ | H |
| O | F | Cl | CH₃ | 0 | 4-CH₂SCH₂CH₃ | H |
| S | H | F | H | 0 | 4-CH₂SCH₂CH=CH₂ | H |
| O | H | F | H | 0 | 4-CH₂SCH₂CH=CH₂ | H |
| S | F | F | H | 0 | 4-CH₂SCH₂CH=CH₂ | H |
| O | F | F | H | 0 | 4-CH₂SCH₂CH=CH₂ | H |
| S | H | Cl | H | 0 | 4-CH₂SCH₂CH=CH₂ | H |
| O | H | Cl | H | 0 | 4-CH₂SCH₂CH=CH₂ | H |
| S | F | Cl | H | 0 | 4-CH₂SCH₂CH=CH₂ | H |
| O | F | Cl | H | 0 | 4-CH₂SCH₂CH=CH₂ | H |
| S | H | F | CH₃ | 0 | 4-CH₂SCH₂CH=CH₂ | H |
| O | H | F | CH₃ | 0 | 4-CH₂SCH₂CH=CH₂ | H |
| S | F | F | CH₃ | 0 | 4-CH₂SCH₂CH=CH₂ | H |
| O | F | F | CH₃ | 0 | 4-CH₂SCH₂CH=CH₂ | H |
| S | H | Cl | CH₃ | 0 | 4-CH₂SCH₂CH=CH₂ | H |
| O | H | Cl | CH₃ | 0 | 4-CH₂SCH₂CH=CH₂ | H |
| S | F | Cl | CH₃ | 0 | 4-CH₂SCH₂CH=CH₂ | H |
| O | F | Cl | CH₃ | 0 | 4-CH₂SCH₂CH=CH₂ | H |
| S | H | F | H | 0 | 4-CO₂H | H |
| O | H | F | H | 0 | 4-CO₂H | H |
| S | F | F | H | 0 | 4-CO₂H | H |
| O | F | F | H | 0 | 4-CO₂H | H |
| S | H | Cl | H | 0 | 4-CO₂H | H |
| O | H | Cl | H | 0 | 4-CO₂H | H |
| S | F | Cl | H | 0 | 4-CO₂H | H |
| O | F | Cl | H | 0 | 4-CO₂H | H |
| S | H | F | CH₃ | 0 | 4-CO₂H | H |
| O | H | F | CH₃ | 0 | 4-CO₂H | H |
| S | F | F | CH₃ | 0 | 4-CO₂H | H |
| O | F | F | CH₃ | 0 | 4-CO₂H | H |
| S | H | Cl | CH₃ | 0 | 4-CO₂H | H |
| O | H | Cl | CH₃ | 0 | 4-CO₂H | H |
| S | F | Cl | CH₃ | 0 | 4-CO₂H | H |
| O | F | Cl | CH₃ | 0 | 4-CO₂H | H |
| S | H | F | H | 1 | H | H |
| O | H | F | H | 1 | H | H |
| S | F | F | H | 1 | H | H |
| O | F | F | H | 1 | H | H |
| S | H | Cl | H | 1 | H | H |
| O | H | Cl | H | 1 | H | H |
| S | F | Cl | H | 1 | H | H |
| O | F | Cl | H | 1 | H | H |
| S | H | F | CH₃ | 1 | H | H |
| O | H | F | CH₃ | 1 | H | H |
| S | F | F | CH₃ | 1 | H | H |
| O | F | F | CH₃ | 1 | H | H |
| S | H | Cl | CH₃ | 1 | H | H |
| O | H | Cl | CH₃ | 1 | H | H |
| S | F | Cl | CH₃ | 1 | H | H |
| O | F | Cl | CH₃ | 1 | H | H |
| S | H | F | H | 1 | 4-CH₃ | H |
| O | H | F | H | 1 | 4-CH₃ | H |
| S | F | F | H | 1 | 4-CH₃ | H |
| O | F | F | H | 1 | 4-CH₃ | H |
| S | H | Cl | H | 1 | 4-CH₃ | H |
| O | H | Cl | H | 1 | 4-CH₃ | H |
| S | F | Cl | H | 1 | 4-CH₃ | H |
| O | F | Cl | H | 1 | 4-CH₃ | H |
| S | H | F | CH₃ | 1 | 4-CH₃ | H |
| O | H | F | CH₃ | 1 | 4-CH₃ | H |
| S | F | F | CH₃ | 1 | 4-CH₃ | H |
| O | F | F | CH₃ | 1 | 4-CH₃ | H |
| S | H | Cl | CH₃ | 1 | 4-CH₃ | H |
| O | H | Cl | CH₃ | 1 | 4-CH₃ | H |
| S | F | Cl | CH₃ | 1 | 4-CH₃ | H |
| O | F | Cl | CH₃ | 1 | 4-CH₃ | H |
| S | H | F | H | 1 | 4,6-Di-CH₃ | H |
| O | H | F | H | 1 | 4,6-Di-CH₃ | H |
| S | F | F | H | 1 | 4,6-Di-CH₃ | H |
| O | F | F | H | 1 | 4,6-Di-CH₃ | H |
| S | H | Cl | H | 1 | 4,6-Di-CH₃ | H |
| O | H | Cl | H | 1 | 4,6-Di-CH₃ | H |
| S | F | Cl | H | 1 | 4,6-Di-CH₃ | H |
| O | F | Cl | H | 1 | 4,6-Di-CH₃ | H |
| S | H | F | CH₃ | 1 | 4,6-Di-CH₃ | H |
| O | H | F | CH₃ | 1 | 4,6-Di-CH₃ | H |
| S | F | F | CH₃ | 1 | 4,6-Di-CH₃ | H |
| O | F | F | CH₃ | 1 | 4,6-Di-CH₃ | H |

TABLE 1-continued

| X | R¹ | R² | R³ | m | R⁵ | R⁴ |
|---|----|----|----|---|-----|----|
| S | H | Cl | CH₃ | 1 | 4,6-Di-CH₃ | H |
| O | H | Cl | CH₃ | 1 | 4,6-Di-CH₃ | H |
| S | F | Cl | CH₃ | 1 | 4,6-Di-CH₃ | H |
| O | F | Cl | CH₃ | 1 | 4,6-Di-CH₃ | H |
| S | H | F | H | 1 | 4-CH₂CH₃ | H |
| O | H | F | H | 1 | 4-CH₂CH₃ | H |
| S | F | F | H | 1 | 4-CH₂CH₃ | H |
| O | F | F | H | 1 | 4-CH₂CH₃ | H |
| S | H | Cl | H | 1 | 4-CH₂CH₃ | H |
| O | H | Cl | H | 1 | 4-CH₂CH₃ | H |
| S | F | Cl | H | 1 | 4-CH₂CH₃ | H |
| O | F | Cl | H | 1 | 4-CH₂CH₃ | H |
| S | H | F | CH₃ | 1 | 4-CH₂CH₃ | H |
| O | H | F | CH₃ | 1 | 4-CH₂CH₃ | H |
| S | F | F | CH₃ | 1 | 4-CH₂CH₃ | H |
| O | F | F | CH₃ | 1 | 4-CH₂CH₃ | H |
| S | H | Cl | CH₃ | 1 | 4-CH₂CH₃ | H |
| O | H | Cl | CH₃ | 1 | 4-CH₂CH₃ | H |
| S | F | Cl | CH₃ | 1 | 4-CH₂CH₃ | H |
| O | F | Cl | CH₃ | 1 | 4-CH₂CH₃ | H |
| S | H | F | H | 1 | 4-CH₂Cl | H |
| O | H | F | H | 1 | 4-CH₂Cl | H |
| S | F | F | H | 1 | 4-CH₂Cl | H |
| O | F | F | H | 1 | 4-CH₂Cl | H |
| S | H | Cl | H | 1 | 4-CH₂Cl | H |
| O | H | Cl | H | 1 | 4-CH₂Cl | H |
| S | F | Cl | H | 1 | 4-CH₂Cl | H |
| O | F | Cl | H | 1 | 4-CH₂Cl | H |
| S | H | F | CH₃ | 1 | 4-CH₂Cl | H |
| O | H | F | CH₃ | 1 | 4-CH₂Cl | H |
| S | F | F | CH₃ | 1 | 4-CH₂Cl | H |
| O | F | F | CH₃ | 1 | 4-CH₂Cl | H |
| S | H | Cl | CH₃ | 1 | 4-CH₂Cl | H |
| O | H | Cl | CH₃ | 1 | 4-CH₂Cl | H |
| S | F | Cl | CH₃ | 1 | 4-CH₂Cl | H |
| O | F | Cl | CH₃ | 1 | 4-CH₂Cl | H |
| S | H | F | H | 1 | 4-CH₂OH | H |
| O | H | F | H | 1 | 4-CH₂OH | H |
| S | F | F | H | 1 | 4-CH₂OH | H |
| O | F | F | H | 1 | 4-CH₂OH | H |
| S | H | Cl | H | 1 | 4-CH₂OH | H |
| O | H | Cl | H | 1 | 4-CH₂OH | H |
| S | F | Cl | H | 1 | 4-CH₂OH | H |
| O | F | Cl | H | 1 | 4-CH₂OH | H |
| S | H | F | CH₃ | 1 | 4-CH₂OH | H |
| O | H | F | CH₃ | 1 | 4-CH₂OH | H |
| S | F | F | CH₃ | 1 | 4-CH₂OH | H |
| O | F | F | CH₃ | 1 | 4-CH₂OH | H |
| S | H | Cl | CH₃ | 1 | 4-CH₂OH | H |
| O | H | Cl | CH₃ | 1 | 4-CH₂OH | H |
| S | F | Cl | CH₃ | 1 | 4-CH₂OH | H |
| O | F | Cl | CH₃ | 1 | 4-CH₂OH | H |
| S | H | F | H | 1 | 4-CH₂OCH₃ | H |
| O | H | F | H | 1 | 4-CH₂OCH₃ | H |
| S | F | F | H | 1 | 4-CH₂OCH₃ | H |
| O | F | F | H | 1 | 4-CH₂OCH₃ | H |
| S | H | Cl | H | 1 | 4-CH₂OCH₃ | H |
| O | H | Cl | H | 1 | 4-CH₂OCH₃ | H |
| S | F | Cl | H | 1 | 4-CH₂OCH₃ | H |
| O | F | Cl | H | 1 | 4-CH₂OCH₃ | H |
| S | H | F | CH₃ | 1 | 4-CH₂OCH₃ | H |
| O | H | F | CH₃ | 1 | 4-CH₂OCH₃ | H |
| S | F | F | CH₃ | 1 | 4-CH₂OCH₃ | H |
| O | F | F | CH₃ | 1 | 4-CH₂OCH₃ | H |
| S | H | Cl | CH₃ | 1 | 4-CH₂OCH₃ | H |
| O | H | Cl | CH₃ | 1 | 4-CH₂OCH₃ | H |
| S | F | Cl | CH₃ | 1 | 4-CH₂OCH₃ | H |
| O | F | Cl | CH₃ | 1 | 4-CH₂OCH₃ | H |
| S | H | F | H | 1 | 4-CH₂OCH₂CH=CH₂ | H |
| O | H | F | H | 1 | 4-CH₂OCH₂CH=CH₂ | H |
| S | F | F | H | 1 | 4-CH₂OCH₂CH=CH₂ | H |
| O | F | F | H | 1 | 4-CH₂OCH₂CH=CH₂ | H |
| S | H | Cl | H | 1 | 4-CH₂OCH₂CH=CH₂ | H |
| O | H | Cl | H | 1 | 4-CH₂OCH₂CH=CH₂ | H |
| S | F | Cl | H | 1 | 4-CH₂OCH₂CH=CH₂ | H |
| O | F | Cl | H | 1 | 4-CH₂OCH₂CH=CH₂ | H |
| S | H | F | CH₃ | 1 | 4-CH₂OCH₂CH=CH₂ | H |
| O | H | F | CH₃ | 1 | 4-CH₂OCH₂CH=CH₂ | H |
| S | F | F | CH₃ | 1 | 4-CH₂OCH₂CH=CH₂ | H |
| O | F | F | CH₃ | 1 | 4-CH₂OCH₂CH=CH₂ | H |
| S | H | Cl | CH₃ | 1 | 4-CH₂OCH₂CH=CH₂ | H |

TABLE 1-continued

| X | R$^1$ | R$^2$ | R$^3$ | m | R$^5$ | R$^4$ |
|---|---|---|---|---|---|---|
| O | H | Cl | CH$_3$ | 1 | 4-CH$_2$OCH$_2$CH=CH$_2$ | H |
| S | F | Cl | CH$_3$ | 1 | 4-CH$_2$OCH$_2$CH=CH$_2$ | H |
| O | F | Cl | CH$_3$ | 1 | 4-CH$_2$OCH$_2$CH=CH$_2$ | H |
| S | H | F | H | 1 | 4-CH$_2$OCH$_2$C≡CH | H |
| O | H | F | H | 1 | 4-CH$_2$OCH$_2$C≡CH | H |
| S | F | F | H | 1 | 4-CH$_2$OCH$_2$C≡CH | H |
| O | F | F | H | 1 | 4-CH$_2$OCH$_2$C≡CH | H |
| S | H | Cl | H | 1 | 4-CH$_2$OCH$_2$C≡CH | H |
| O | H | Cl | H | 1 | 4-CH$_2$OCH$_2$C≡CH | H |
| S | F | Cl | H | 1 | 4-CH$_2$OCH$_2$C≡CH | H |
| O | F | Cl | H | 1 | 4-CH$_2$OCH$_2$C≡CH | H |
| S | H | F | CH$_3$ | 1 | 4-CH$_2$OCH$_2$C≡CH | H |
| O | H | F | CH$_3$ | 1 | 4-CH$_2$OCH$_2$C≡CH | H |
| S | F | F | CH$_3$ | 1 | 4-CH$_2$OCH$_2$C≡CH | H |
| O | F | F | CH$_3$ | 1 | 4-CH$_2$OCH$_2$C≡CH | H |
| S | H | Cl | CH$_3$ | 1 | 4-CH$_2$OCH$_2$C≡CH | H |
| O | H | Cl | CH$_3$ | 1 | 4-CH$_2$OCH$_2$C≡CH | H |
| S | F | Cl | CH$_3$ | 1 | 4-CH$_2$OCH$_2$C≡CH | H |
| O | F | Cl | CH$_3$ | 1 | 4-CH$_2$OCH$_2$C≡CH | H |
| S | H | F | H | 1 | 4-CH$_2$OCOCH$_3$ | H |
| O | H | F | H | 1 | 4-CH$_2$OCOCH$_3$ | H |
| S | F | F | H | 1 | 4-CH$_2$OCOCH$_3$ | H |
| O | F | F | H | 1 | 4-CH$_2$OCOCH$_3$ | H |
| S | H | Cl | H | 1 | 4-CH$_2$OCOCH$_3$ | H |
| O | H | Cl | H | 1 | 4-CH$_2$OCOCH$_3$ | H |
| S | F | Cl | H | 1 | 4-CH$_2$OCOCH$_3$ | H |
| O | F | Cl | H | 1 | 4-CH$_2$OCOCH$_3$ | H |
| S | H | F | CH$_3$ | 1 | 4-CH$_2$OCOCH$_3$ | H |
| O | H | F | CH$_3$ | 1 | 4-CH$_2$OCOCH$_3$ | H |
| S | F | F | CH$_3$ | 1 | 4-CH$_2$OCOCH$_3$ | H |
| O | F | F | CH$_3$ | 1 | 4-CH$_2$OCOCH$_3$ | H |
| S | H | Cl | CH$_3$ | 1 | 4-CH$_2$OCOCH$_3$ | H |
| O | H | Cl | CH$_3$ | 1 | 4-CH$_2$OCOCH$_3$ | H |
| S | F | Cl | CH$_3$ | 1 | 4-CH$_2$OCOCH$_3$ | H |
| O | F | Cl | CH$_3$ | 1 | 4-CH$_2$OCOCH$_3$ | H |
| S | H | F | H | 1 | 4-CH$_2$OCH$_2$CO$_2$CH$_3$ | H |
| O | H | F | H | 1 | 4-CH$_2$OCH$_2$CO$_2$CH$_3$ | H |
| S | F | F | H | 1 | 4-CH$_2$OCH$_2$CO$_2$CH$_3$ | H |
| O | F | F | H | 1 | 4-CH$_2$OCH$_2$CO$_2$CH$_3$ | H |
| S | H | Cl | H | 1 | 4-CH$_2$OCH$_2$CO$_2$CH$_3$ | H |
| O | H | Cl | H | 1 | 4-CH$_2$OCH$_2$CO$_2$CH$_3$ | H |
| S | F | Cl | H | 1 | 4-CH$_2$OCH$_2$CO$_2$CH$_3$ | H |
| O | F | Cl | H | 1 | 4-CH$_2$OCH$_2$CO$_2$CH$_3$ | H |
| S | H | F | CH$_3$ | 1 | 4-CH$_2$OCH$_2$CO$_2$CH$_3$ | H |
| O | H | F | CH$_3$ | 1 | 4-CH$_2$OCH$_2$CO$_2$CH$_3$ | H |
| S | F | F | CH$_3$ | 1 | 4-CH$_2$OCH$_2$CO$_2$CH$_3$ | H |
| O | F | F | CH$_3$ | 1 | 4-CH$_2$OCH$_2$CO$_2$CH$_3$ | H |
| S | H | Cl | CH$_3$ | 1 | 4-CH$_2$OCH$_2$CO$_2$CH$_3$ | H |
| O | H | Cl | CH$_3$ | 1 | 4-CH$_2$OCH$_2$CO$_2$CH$_3$ | H |
| S | F | Cl | CH$_3$ | 1 | 4-CH$_2$OCH$_2$CO$_2$CH$_3$ | H |
| O | F | Cl | CH$_3$ | 1 | 4-CH$_2$OCH$_2$CO$_2$CH$_3$ | H |
| S | H | F | H | 1 | 4-CH$_2$CO$_2$CH$_3$ | H |
| O | H | F | H | 1 | 4-CH$_2$CO$_2$CH$_3$ | H |
| S | F | F | H | 1 | 4-CH$_2$CO$_2$CH$_3$ | H |
| O | F | F | H | 1 | 4-CH$_2$CO$_2$CH$_3$ | H |
| S | H | Cl | H | 1 | 4-CH$_2$CO$_2$CH$_3$ | H |
| O | H | Cl | H | 1 | 4-CH$_2$CO$_2$CH$_3$ | H |
| S | F | Cl | H | 1 | 4-CH$_2$CO$_2$CH$_3$ | H |
| O | F | Cl | H | 1 | 4-CH$_2$CO$_2$CH$_3$ | H |
| S | H | F | CH$_3$ | 1 | 4-CH$_2$CO$_2$CH$_3$ | H |
| O | H | F | CH$_3$ | 1 | 4-CH$_2$CO$_2$CH$_3$ | H |
| S | F | F | CH$_3$ | 1 | 4-CH$_2$CO$_2$CH$_3$ | H |
| O | F | F | CH$_3$ | 1 | 4-CH$_2$CO$_2$CH$_3$ | H |
| S | H | Cl | CH$_3$ | 1 | 4-CH$_2$CO$_2$CH$_3$ | H |
| O | H | Cl | CH$_3$ | 1 | 4-CH$_2$CO$_2$CH$_3$ | H |
| S | F | Cl | CH$_3$ | 1 | 4-CH$_2$CO$_2$CH$_3$ | H |
| O | F | Cl | CH$_3$ | 1 | 4-CH$_2$CO$_2$CH$_3$ | H |
| S | H | F | H | 1 | 4-CH$_2$SH | H |
| O | H | F | H | 1 | 4-CH$_2$SH | H |
| S | F | F | H | 1 | 4-CH$_2$SH | H |
| O | F | F | H | 1 | 4-CH$_2$SH | H |
| S | H | Cl | H | 1 | 4-CH$_2$SH | H |
| O | H | Cl | H | 1 | 4-CH$_2$SH | H |
| S | F | Cl | H | 1 | 4-CH$_2$SH | H |
| O | F | Cl | H | 1 | 4-CH$_2$SH | H |
| S | H | F | CH$_3$ | 1 | 4-CH$_2$SH | H |
| O | H | F | CH$_3$ | 1 | 4-CH$_2$SH | H |
| S | F | F | CH$_3$ | 1 | 4-CH$_2$SH | H |
| O | F | F | CH$_3$ | 1 | 4-CH$_2$SH | H |
| S | H | Cl | CH$_3$ | 1 | 4-CH$_2$SH | H |
| O | H | Cl | CH$_3$ | 1 | 4-CH$_2$SH | H |

TABLE 1-continued

| X | R¹ | R² | R³ | m | R⁵ | R⁴ |
|---|----|----|-----|---|-----|-----|
| S | F | Cl | CH₃ | 1 | 4-CH₂SH | H |
| O | F | Cl | CH₃ | 1 | 4-CH₂SH | H |
| S | H | F | H | 1 | 4-CH₂SCH₂CH₃ | H |
| O | H | F | H | 1 | 4-CH₂SCH₂CH₃ | H |
| S | F | F | H | 1 | 4-CH₂SCH₂CH₃ | H |
| O | F | F | H | 1 | 4-CH₂SCH₂CH₃ | H |
| S | H | Cl | H | 1 | 4-CH₂SCH₂CH₃ | H |
| O | H | Cl | H | 1 | 4-CH₂SCH₂CH₃ | H |
| S | F | Cl | H | 1 | 4-CH₂SCH₂CH₃ | H |
| O | F | Cl | H | 1 | 4-CH₂SCH₂CH₃ | H |
| S | H | F | CH₃ | 1 | 4-CH₂SCH₂CH₃ | H |
| O | H | F | CH₃ | 1 | 4-CH₂SCH₂CH₃ | H |
| S | F | F | CH₃ | 1 | 4-CH₂SCH₂CH₃ | H |
| O | F | F | CH₃ | 1 | 4-CH₂SCH₂CH₃ | H |
| S | H | Cl | CH₃ | 1 | 4-CH₂SCH₂CH₃ | H |
| O | H | Cl | CH₃ | 1 | 4-CH₂SCH₂CH₃ | H |
| S | F | Cl | CH₃ | 1 | 4-CH₂SCH₂CH₃ | H |
| O | F | Cl | CH₃ | 1 | 4-CH₂SCH₂CH₃ | H |
| S | H | F | H | 1 | 4-CH₂SCH₂CH=CH₂ | H |
| O | H | F | H | 1 | 4-CH₂SCH₂CH=CH₂ | H |
| S | F | F | H | 1 | 4-CH₂SCH₂CH=CH₂ | H |
| O | F | F | H | 1 | 4-CH₂SCH₂CH=CH₂ | H |
| S | H | Cl | H | 1 | 4-CH₂SCH₂CH=CH₂ | H |
| O | H | Cl | H | 1 | 4-CH₂SCH₂CH=CH₂ | H |
| S | F | Cl | H | 1 | 4-CH₂SCH₂CH=CH₂ | H |
| O | F | Cl | H | 1 | 4-CH₂SCH₂CH=CH₂ | H |
| S | H | F | CH₃ | 1 | 4-CH₂SCH₂CH=CH₂ | H |
| O | H | F | CH₃ | 1 | 4-CH₂SCH₂CH=CH₂ | H |
| S | F | F | CH₃ | 1 | 4-CH₂SCH₂CH=CH₂ | H |
| O | F | F | CH₃ | 1 | 4-CH₂SCH₂CH=CH₂ | H |
| S | H | Cl | CH₃ | 1 | 4-CH₂SCH₂CH=CH₂ | H |
| O | H | Cl | CH₃ | 1 | 4-CH₂SCH₂CH=CH₂ | H |
| S | F | Cl | CH₃ | 1 | 4-CH₂SCH₂CH=CH₂ | H |
| O | F | Cl | CH₃ | 1 | 4-CH₂SCH₂CH=CH₂ | H |
| S | H | F | H | 1 | 4-CO₂H | H |
| O | H | F | H | 1 | 4-CO₂H | H |
| S | F | F | H | 1 | 4-CO₂H | H |
| O | F | F | H | 1 | 4-CO₂H | H |
| S | H | Cl | H | 1 | 4-CO₂H | H |
| O | H | Cl | H | 1 | 4-CO₂H | H |
| S | F | Cl | H | 1 | 4-CO₂H | H |
| O | F | Cl | H | 1 | 4-CO₂H | H |
| S | H | F | CH₃ | 1 | 4-CO₂H | H |
| O | H | F | CH₃ | 1 | 4-CO₂H | H |
| S | F | F | CH₃ | 1 | 4-CO₂H | H |
| O | F | F | CH₃ | 1 | 4-CO₂H | H |
| S | H | Cl | CH₃ | 1 | 4-CO₂H | H |
| O | H | Cl | CH₃ | 1 | 4-CO₂H | H |
| S | F | Cl | CH₃ | 1 | 4-CO₂H | H |
| O | F | Cl | CH₃ | 1 | 4-CO₂H | H |
| S | H | F | H | 0 | H | CO₂CH₃ |
| O | H | F | H | 0 | H | CO₂CH₃ |
| S | F | F | H | 0 | H | CO₂CH₃ |
| O | F | F | H | 0 | H | CO₂CH₃ |
| S | H | Cl | H | 0 | H | CO₂CH₃ |
| O | H | Cl | H | 0 | H | CO₂CH₃ |
| S | F | Cl | H | 0 | H | CO₂CH₃ |
| O | F | Cl | H | 0 | H | CO₂CH₃ |
| S | H | F | CH₃ | 0 | H | CO₂CH₃ |
| O | H | F | CH₃ | 0 | H | CO₂CH₃ |
| S | F | F | CH₃ | 0 | H | CO₂CH₃ |
| O | F | F | CH₃ | 0 | H | CO₂CH₃ |
| S | H | Cl | CH₃ | 0 | H | CO₂CH₃ |
| O | H | Cl | CH₃ | 0 | H | CO₂CH₃ |
| S | F | Cl | CH₃ | 0 | H | CO₂CH₃ |
| O | F | Cl | CH₃ | 0 | H | CO₂CH₃ |
| S | H | F | H | 0 | H | CO₂CH₂CH₃ |
| O | H | F | H | 0 | H | CO₂CH₂CH₃ |
| S | F | F | H | 0 | H | CO₂CH₂CH₃ |
| O | F | F | H | 0 | H | CO₂CH₂CH₃ |
| S | H | Cl | H | 0 | H | CO₂CH₂CH₃ |
| O | H | Cl | H | 0 | H | CO₂CH₂CH₃ |
| S | F | Cl | H | 0 | H | CO₂CH₂CH₃ |
| O | F | Cl | H | 0 | H | CO₂CH₂CH₃ |
| S | H | F | CH₃ | 0 | H | CO₂CH₂CH₃ |
| O | H | F | CH₃ | 0 | H | CO₂CH₂CH₃ |
| S | F | F | CH₃ | 0 | H | CO₂CH₂CH₃ |
| O | F | F | CH₃ | 0 | H | CO₂CH₂CH₃ |
| S | H | Cl | CH₃ | 0 | H | CO₂CH₂CH₃ |
| O | H | Cl | CH₃ | 0 | H | CO₂CH₂CH₃ |
| S | F | Cl | CH₃ | 0 | H | CO₂CH₂CH₃ |

TABLE 1-continued

| X | R$^1$ | R$^2$ | R$^3$ | m | R$^5$ | R$^4$ |
|---|---|---|---|---|---|---|
| O | F | Cl | CH$_3$ | 0 | H | CO$_2$CH$_2$CH$_3$ |
| S | H | F | H | 0 | H | CO$_2$(CH$_2$)$_2$CH$_3$ |
| O | H | F | H | 0 | H | CO$_2$(CH$_2$)$_2$CH$_3$ |
| S | F | F | H | 0 | H | CO$_2$(CH$_2$)$_2$CH$_3$ |
| O | F | F | H | 0 | H | CO$_2$(CH$_2$)$_2$CH$_3$ |
| S | H | Cl | H | 0 | H | CO$_2$(CH$_2$)$_2$CH$_3$ |
| O | H | Cl | H | 0 | H | CO$_2$(CH$_2$)$_2$CH$_3$ |
| S | F | Cl | H | 0 | H | CO$_2$(CH$_2$)$_2$CH$_3$ |
| O | F | Cl | H | 0 | H | CO$_2$(CH$_2$)$_2$CH$_3$ |
| S | H | F | CH$_3$ | 0 | H | CO$_2$(CH$_2$)$_2$CH$_3$ |
| O | H | F | CH$_3$ | 0 | H | CO$_2$(CH$_2$)$_2$CH$_3$ |
| S | F | F | CH$_3$ | 0 | H | CO$_2$(CH$_2$)$_2$CH$_3$ |
| O | F | F | CH$_3$ | 0 | H | CO$_2$(CH$_2$)$_2$CH$_3$ |
| S | H | Cl | CH$_3$ | 0 | H | CO$_2$(CH$_2$)$_2$CH$_3$ |
| O | H | Cl | CH$_3$ | 0 | H | CO$_2$(CH$_2$)$_2$CH$_3$ |
| S | F | Cl | CH$_3$ | 0 | H | CO$_2$(CH$_2$)$_2$CH$_3$ |
| O | F | Cl | CH$_3$ | 0 | H | CO$_2$(CH$_2$)$_2$CH$_3$ |
| S | H | F | H | 0 | H | CO$_2$CH(CH$_3$)$_2$ |
| O | H | F | H | 0 | H | CO$_2$CH(CH$_3$)$_2$ |
| S | F | F | H | 0 | H | CO$_2$CH(CH$_3$)$_2$ |
| O | F | F | H | 0 | H | CO$_2$CH(CH$_3$)$_2$ |
| S | H | Cl | H | 0 | H | CO$_2$CH(CH$_3$)$_2$ |
| O | H | Cl | H | 0 | H | CO$_2$CH(CH$_3$)$_2$ |
| S | F | Cl | H | 0 | H | CO$_2$CH(CH$_3$)$_2$ |
| O | F | Cl | H | 0 | H | CO$_2$CH(CH$_3$)$_2$ |
| S | H | F | CH$_3$ | 0 | H | CO$_2$CH(CH$_3$)$_2$ |
| O | H | F | CH$_3$ | 0 | H | CO$_2$CH(CH$_3$)$_2$ |
| S | F | F | CH$_3$ | 0 | H | CO$_2$CH(CH$_3$)$_2$ |
| O | F | F | CH$_3$ | 0 | H | CO$_2$CH(CH$_3$)$_2$ |
| S | H | Cl | CH$_3$ | 0 | H | CO$_2$CH(CH$_3$)$_2$ |
| O | H | Cl | CH$_3$ | 0 | H | CO$_2$CH(CH$_3$)$_2$ |
| S | F | Cl | CH$_3$ | 0 | H | CO$_2$CH(CH$_3$)$_2$ |
| O | F | Cl | CH$_3$ | 0 | H | CO$_2$CH(CH$_3$)$_2$ |
| S | H | F | H | 0 | H | CO$_2$(CH$_2$)$_3$CH$_3$ |
| O | H | F | H | 0 | H | CO$_2$(CH$_2$)$_3$CH$_3$ |
| S | F | F | H | 0 | H | CO$_2$(CH$_2$)$_3$CH$_3$ |
| O | F | F | H | 0 | H | CO$_2$(CH$_2$)$_3$CH$_3$ |
| S | H | Cl | H | 0 | H | CO$_2$(CH$_2$)$_3$CH$_3$ |
| O | H | Cl | H | 0 | H | CO$_2$(CH$_2$)$_3$CH$_3$ |
| S | F | Cl | H | 0 | H | CO$_2$(CH$_2$)$_3$CH$_3$ |
| O | F | Cl | H | 0 | H | CO$_2$(CH$_2$)$_3$CH$_3$ |
| S | H | F | CH$_3$ | 0 | H | CO$_2$(CH$_2$)$_3$CH$_3$ |
| O | H | F | CH$_3$ | 0 | H | CO$_2$(CH$_2$)$_3$CH$_3$ |
| S | F | F | CH$_3$ | 0 | H | CO$_2$(CH$_2$)$_3$CH$_3$ |
| O | F | F | CH$_3$ | 0 | H | CO$_2$(CH$_2$)$_3$CH$_3$ |
| S | H | Cl | CH$_3$ | 0 | H | CO$_2$(CH$_2$)$_3$CH$_3$ |
| O | H | Cl | CH$_3$ | 0 | H | CO$_2$(CH$_2$)$_3$CH$_3$ |
| S | F | Cl | CH$_3$ | 0 | H | CO$_2$(CH$_2$)$_3$CH$_3$ |
| O | F | Cl | CH$_3$ | 0 | H | CO$_2$(CH$_2$)$_3$CH$_3$ |
| S | H | F | H | 0 | H | CO$_2$(CH$_2$)$_2$OCH$_3$ |
| O | H | F | H | 0 | H | CO$_2$(CH$_2$)$_2$OCH$_3$ |
| S | F | F | H | 0 | H | CO$_2$(CH$_2$)$_2$OCH$_3$ |
| O | F | F | H | 0 | H | CO$_2$(CH$_2$)$_2$OCH$_3$ |
| S | H | Cl | H | 0 | H | CO$_2$(CH$_2$)$_2$OCH$_3$ |
| O | H | Cl | H | 0 | H | CO$_2$(CH$_2$)$_2$OCH$_3$ |
| S | F | Cl | H | 0 | H | CO$_2$(CH$_2$)$_2$OCH$_3$ |
| O | F | Cl | H | 0 | H | CO$_2$(CH$_2$)$_2$OCH$_3$ |
| S | H | F | CH$_3$ | 0 | H | CO$_2$(CH$_2$)$_2$OCH$_3$ |
| O | H | F | CH$_3$ | 0 | H | CO$_2$(CH$_2$)$_2$OCH$_3$ |
| S | F | F | CH$_3$ | 0 | H | CO$_2$(CH$_2$)$_2$OCH$_3$ |
| O | F | F | CH$_3$ | 0 | H | CO$_2$(CH$_2$)$_2$OCH$_3$ |
| S | H | Cl | CH$_3$ | 0 | H | CO$_2$(CH$_2$)$_2$OCH$_3$ |
| O | H | Cl | CH$_3$ | 0 | H | CO$_2$(CH$_2$)$_2$OCH$_3$ |
| S | F | Cl | CH$_3$ | 0 | H | CO$_2$(CH$_2$)$_2$OCH$_3$ |
| O | F | Cl | CH$_3$ | 0 | H | CO$_2$(CH$_2$)$_2$OCH$_3$ |
| S | H | F | H | 0 | H | CO$_2$(CH$_2$)$_2$OCH$_2$CH$_3$ |
| O | H | F | H | 0 | H | CO$_2$(CH$_2$)$_2$OCH$_2$CH$_3$ |
| S | F | F | H | 0 | H | CO$_2$(CH$_2$)$_2$OCH$_2$CH$_3$ |
| O | F | F | H | 0 | H | CO$_2$(CH$_2$)$_2$OCH$_2$CH$_3$ |
| S | H | Cl | H | 0 | H | CO$_2$(CH$_2$)$_2$OCH$_2$CH$_3$ |
| O | H | Cl | H | 0 | H | CO$_2$(CH$_2$)$_2$OCH$_2$CH$_3$ |
| S | F | Cl | H | 0 | H | CO$_2$(CH$_2$)$_2$OCH$_2$CH$_3$ |
| O | F | Cl | H | 0 | H | CO$_2$(CH$_2$)$_2$OCH$_2$CH$_3$ |
| S | H | F | CH$_3$ | 0 | H | CO$_2$(CH$_2$)$_2$OCH$_2$CH$_3$ |
| O | H | F | CH$_3$ | 0 | H | CO$_2$(CH$_2$)$_2$OCH$_2$CH$_3$ |
| S | F | F | CH$_3$ | 0 | H | CO$_2$(CH$_2$)$_2$OCH$_2$CH$_3$ |
| O | F | F | CH$_3$ | 0 | H | CO$_2$(CH$_2$)$_2$OCH$_2$CH$_3$ |
| S | H | Cl | CH$_3$ | 0 | H | CO$_2$(CH$_2$)$_2$OCH$_2$CH$_3$ |
| O | H | Cl | CH$_3$ | 0 | H | CO$_2$(CH$_2$)$_2$OCH$_2$CH$_3$ |
| S | F | Cl | CH$_3$ | 0 | H | CO$_2$(CH$_2$)$_2$OCH$_2$CH$_3$ |
| O | F | Cl | CH$_3$ | 0 | H | CO$_2$(CH$_2$)$_2$OCH$_2$CH$_3$ |

TABLE 1-continued

| X | R¹ | R² | R³ | m | R⁵ | R⁴ |
|---|----|----|----|---|----|----|
| S | H | F | H | 0 | 4-CH₃ | CO₂CH₃ |
| O | H | F | H | 0 | 4-CH₃ | CO₂CH₃ |
| S | F | F | H | 0 | 4-CH₃ | CO₂CH₃ |
| O | F | F | H | 0 | 4-CH₃ | CO₂CH₃ |
| S | H | Cl | H | 0 | 4-CH₃ | CO₂CH₃ |
| O | H | Cl | H | 0 | 4-CH₃ | CO₂CH₃ |
| S | F | Cl | H | 0 | 4-CH₃ | CO₂CH₃ |
| O | F | Cl | H | 0 | 4-CH₃ | CO₂CH₃ |
| S | H | F | CH₃ | 0 | 4-CH₃ | CO₂CH₃ |
| O | H | F | CH₃ | 0 | 4-CH₃ | CO₂CH₃ |
| S | F | F | CH₃ | 0 | 4-CH₃ | CO₂CH₃ |
| O | F | F | CH₃ | 0 | 4-CH₃ | CO₂CH₃ |
| S | H | Cl | CH₃ | 0 | 4-CH₃ | CO₂CH₃ |
| O | H | Cl | CH₃ | 0 | 4-CH₃ | CO₂CH₃ |
| S | F | Cl | CH₃ | 0 | 4-CH₃ | CO₂CH₃ |
| O | F | Cl | CH₃ | 0 | 4-CH₃ | CO₂CH₃ |
| S | H | F | H | 0 | 4-CH₃ | CO₂CH₂CH₃ |
| O | H | F | H | 0 | 4-CH₃ | CO₂CH₂CH₃ |
| S | F | F | H | 0 | 4-CH₃ | CO₂CH₂CH₃ |
| O | F | F | H | 0 | 4-CH₃ | CO₂CH₂CH₃ |
| S | H | Cl | H | 0 | 4-CH₃ | CO₂CH₂CH₃ |
| O | H | Cl | H | 0 | 4-CH₃ | CO₂CH₂CH₃ |
| S | F | Cl | H | 0 | 4-CH₃ | CO₂CH₂CH₃ |
| O | F | Cl | H | 0 | 4-CH₃ | CO₂CH₂CH₃ |
| S | H | F | CH₃ | 0 | 4-CH₃ | CO₂CH₂CH₃ |
| O | H | F | CH₃ | 0 | 4-CH₃ | CO₂CH₂CH₃ |
| S | F | F | CH₃ | 0 | 4-CH₃ | CO₂CH₂CH₃ |
| O | F | F | CH₃ | 0 | 4-CH₃ | CO₂CH₂CH₃ |
| S | H | Cl | CH₃ | 0 | 4-CH₃ | CO₂CH₂CH₃ |
| O | H | Cl | CH₃ | 0 | 4-CH₃ | CO₂CH₂CH₃ |
| S | F | Cl | CH₃ | 0 | 4-CH₃ | CO₂CH₂CH₃ |
| O | F | Cl | CH₃ | 0 | 4-CH₃ | CO₂CH₂CH₃ |
| S | H | F | H | 0 | 4-CH₃ | CO₂(CH₂)₂CH₃ |
| O | H | F | H | 0 | 4-CH₃ | CO₂(CH₂)₂CH₃ |
| S | F | F | H | 0 | 4-CH₃ | CO₂(CH₂)₂CH₃ |
| O | F | F | H | 0 | 4-CH₃ | CO₂(CH₂)₂CH₃ |
| S | H | Cl | H | 0 | 4-CH₃ | CO₂(CH₂)₂CH₃ |
| O | H | Cl | H | 0 | 4-CH₃ | CO₂(CH₂)₂CH₃ |
| S | F | Cl | H | 0 | 4-CH₃ | CO₂(CH₂)₂CH₃ |
| O | F | Cl | H | 0 | 4-CH₃ | CO₂(CH₂)₂CH₃ |
| S | H | F | CH₃ | 0 | 4-CH₃ | CO₂(CH₂)₂CH₃ |
| O | H | F | CH₃ | 0 | 4-CH₃ | CO₂(CH₂)₂CH₃ |
| S | F | F | CH₃ | 0 | 4-CH₃ | CO₂(CH₂)₂CH₃ |
| O | F | F | CH₃ | 0 | 4-CH₃ | CO₂(CH₂)₂CH₃ |
| S | H | Cl | CH₃ | 0 | 4-CH₃ | CO₂(CH₂)₂CH₃ |
| O | H | Cl | CH₃ | 0 | 4-CH₃ | CO₂(CH₂)₂CH₃ |
| S | F | Cl | CH₃ | 0 | 4-CH₃ | CO₂(CH₂)₂CH₃ |
| O | F | Cl | CH₃ | 0 | 4-CH₃ | CO₂(CH₂)₂CH₃ |
| S | H | F | H | 0 | 4-CH₃ | CO₂CH(CH₃)₂ |
| O | H | F | H | 0 | 4-CH₃ | CO₂CH(CH₃)₂ |
| S | F | F | H | 0 | 4-CH₃ | CO₂CH(CH₃)₂ |
| O | F | F | H | 0 | 4-CH₃ | CO₂CH(CH₃)₂ |
| S | H | Cl | H | 0 | 4-CH₃ | CO₂CH(CH₃)₂ |
| O | H | Cl | H | 0 | 4-CH₃ | CO₂CH(CH₃)₂ |
| S | F | Cl | H | 0 | 4-CH₃ | CO₂CH(CH₃)₂ |
| O | F | Cl | H | 0 | 4-CH₃ | CO₂CH(CH₃)₂ |
| S | H | F | CH₃ | 0 | 4-CH₃ | CO₂CH(CH₃)₂ |
| O | H | F | CH₃ | 0 | 4-CH₃ | CO₂CH(CH₃)₂ |
| S | F | F | CH₃ | 0 | 4-CH₃ | CO₂CH(CH₃)₂ |
| O | F | F | CH₃ | 0 | 4-CH₃ | CO₂CH(CH₃)₂ |
| S | H | Cl | CH₃ | 0 | 4-CH₃ | CO₂CH(CH₃)₂ |
| O | H | Cl | CH₃ | 0 | 4-CH₃ | CO₂CH(CH₃)₂ |
| S | F | Cl | CH₃ | 0 | 4-CH₃ | CO₂CH(CH₃)₂ |
| O | F | Cl | CH₃ | 0 | 4-CH₃ | CO₂CH(CH₃)₂ |
| S | H | F | H | 0 | 4-CH₃ | CO₂(CH₂)₃CH₃ |
| O | H | F | H | 0 | 4-CH₃ | CO₂(CH₂)₃CH₃ |
| S | F | F | H | 0 | 4-CH₃ | CO₂(CH₂)₃CH₃ |
| O | F | F | H | 0 | 4-CH₃ | CO₂(CH₂)₃CH₃ |
| S | H | Cl | H | 0 | 4-CH₃ | CO₂(CH₂)₃CH₃ |
| O | H | Cl | H | 0 | 4-CH₃ | CO₂(CH₂)₃CH₃ |
| S | F | Cl | H | 0 | 4-CH₃ | CO₂(CH₂)₃CH₃ |
| O | F | Cl | H | 0 | 4-CH₃ | CO₂(CH₂)₃CH₃ |
| S | H | F | CH₃ | 0 | 4-CH₃ | CO₂(CH₂)₃CH₃ |
| O | H | F | CH₃ | 0 | 4-CH₃ | CO₂(CH₂)₃CH₃ |
| S | F | F | CH₃ | 0 | 4-CH₃ | CO₂(CH₂)₃CH₃ |
| O | F | F | CH₃ | 0 | 4-CH₃ | CO₂(CH₂)₃CH₃ |
| S | H | Cl | CH₃ | 0 | 4-CH₃ | CO₂(CH₂)₃CH₃ |
| O | H | Cl | CH₃ | 0 | 4-CH₃ | CO₂(CH₂)₃CH₃ |
| S | F | Cl | CH₃ | 0 | 4-CH₃ | CO₂(CH₂)₃CH₃ |
| O | F | Cl | CH₃ | 0 | 4-CH₃ | CO₂(CH₂)₃CH₃ |
| S | H | F | H | 0 | 4-CH₃ | CO₂(CH₂)₂OCH₃ |

TABLE 1-continued

| X | R¹ | R² | R³ | m | R⁵ | R⁴ |
|---|----|----|----|---|----|----|
| O | H | F | H | 0 | 4-CH₃ | CO₂(CH₂)₂OCH₃ |
| S | F | F | H | 0 | 4-CH₃ | CO₂(CH₂)₂OCH₃ |
| O | F | F | H | 0 | 4-CH₃ | CO₂(CH₂)₂OCH₃ |
| S | H | Cl | H | 0 | 4-CH₃ | CO₂(CH₃)₂OCH₃ |
| O | H | Cl | H | 0 | 4-CH₃ | CO₂(CH₂)₂OCH₃ |
| S | F | Cl | H | 0 | 4-CH₃ | CO₂(CH₂)₂OCH₃ |
| O | F | Cl | H | 0 | 4-CH₃ | CO₂(CH₂)₂OCH₃ |
| S | H | F | CH₃ | 0 | 4-CH₃ | CO₂(CH₂)₂OCH₃ |
| O | H | F | CH₃ | 0 | 4-CH₃ | CO₂(CH₂)₂OCH₃ |
| S | F | F | CH₃ | 0 | 4-CH₃ | CO₂(CH₂)₂OCH₃ |
| O | F | F | CH₃ | 0 | 4-CH₃ | CO₂(CH₂)₂OCH₃ |
| S | H | Cl | CH₃ | 0 | 4-CH₃ | CO₂(CH₂)₂OCH₃ |
| O | H | Cl | CH₃ | 0 | 4-CH₃ | CO₂(CH₂)₂OCH₃ |
| S | F | Cl | CH₃ | 0 | 4-CH₃ | CO₂(CH₂)₂OCH₃ |
| O | F | Cl | CH₃ | 0 | 4-CH₃ | CO₂(CH₂)₂OCH₃ |
| S | H | F | H | 0 | 4-CH₃ | CO₂(CH₂)₂OCH₂CH₃ |
| O | H | F | H | 0 | 4-CH₃ | CO₂(CH₂)₂OCH₂CH₃ |
| S | F | F | H | 0 | 4-CH₃ | CO₂(CH₂)₂OCH₂CH₃ |
| O | F | F | H | 0 | 4-CH₃ | CO₂(CH₂)₂OCH₂CH₃ |
| S | H | Cl | H | 0 | 4-CH₃ | CO₂(CH₂)₂OCH₂CH₃ |
| O | H | Cl | H | 0 | 4-CH₃ | CO₂(CH₂)₂OCH₂CH₃ |
| S | F | Cl | H | 0 | 4-CH₃ | CO₂(CH₂)₂OCH₂CH₃ |
| O | F | Cl | H | 0 | 4-CH₃ | CO₂(CH₂)₂OCH₂CH₃ |
| S | H | F | CH₃ | 0 | 4-CH₃ | CO₂(CH₂)₂OCH₂CH₃ |
| O | H | F | CH₃ | 0 | 4-CH₃ | CO₂(CH₂)₂OCH₂CH₃ |
| S | F | F | CH₃ | 0 | 4-CH₃ | CO₂(CH₂)₂OCH₂CH₃ |
| O | F | F | CH₃ | 0 | 4-CH₃ | CO₂(CH₂)₂OCH₂CH₃ |
| S | H | Cl | CH₃ | 0 | 4-CH₃ | CO₂(CH₂)₂OCH₂CH₃ |
| O | H | Cl | CH₃ | 0 | 4-CH₃ | CO₂(CH₂)₂OCH₂CH₃ |
| S | F | Cl | CH₃ | 0 | 4-CH₃ | CO₂(CH₂)₂OCH₂CH₃ |
| O | F | Cl | CH₃ | 0 | 4-CH₃ | CO₂(CH₂)₂OCH₂CH₃ |
| S | H | F | H | 0 | 5-CH₃ | CO₂CH₃ |
| C | H | F | H | 0 | 5-CH₃ | CO₂CH₃ |
| S | F | F | H | 0 | 5-CH₃ | CO₂CH₃ |
| O | F | F | H | 0 | 5-CH₃ | CO₂CH₃ |
| S | H | Cl | H | 0 | 5-CH₃ | CO₂CH₃ |
| O | H | Cl | H | 0 | 5-CH₃ | CO₂CH₃ |
| S | F | Cl | H | 0 | 5-CH₃ | CO₂CH₃ |
| O | F | Cl | H | 0 | 5-CH₃ | CO₂CH₃ |
| S | H | F | CH₃ | 0 | 5-CH₃ | CO₂CH₃ |
| O | H | F | CH₃ | 0 | 5-CH₃ | CO₂CH₃ |
| S | F | F | CH₃ | 0 | 5-CH₃ | CO₂CH₃ |
| O | F | F | CH₃ | 0 | 5-CH₃ | CO₂CH₃ |
| S | H | Cl | CH₃ | 0 | 5-CH₃ | CO₂CH₃ |
| O | H | Cl | CH₃ | 0 | 5-CH₃ | CO₂CH₃ |
| S | F | Cl | CH₃ | 0 | 5-CH₃ | CO₂CH₃ |
| O | F | Cl | CH₃ | 0 | 5-CH₃ | CO₂CH₃ |
| S | H | F | H | 0 | 5-CH₃ | CO₂CH₂CH₃ |
| O | H | F | H | 0 | 5-CH₃ | CO₂CH₂CH₃ |
| S | F | F | H | 0 | 5-CH₃ | CO₂CH₂CH₃ |
| O | F | F | H | 0 | 5-CH₃ | CO₂CH₂CH₃ |
| S | H | Cl | H | 0 | 5-CH₃ | CO₂CH₂CH₃ |
| O | H | Cl | H | 0 | 5-CH₃ | CO₂CH₂CH₃ |
| S | F | Cl | H | 0 | 5-CH₃ | CO₂CH₂CH₃ |
| O | F | Cl | H | 0 | 5-CH₃ | CO₂CH₂CH₃ |
| S | H | F | CH₃ | 0 | 5-CH₃ | CO₂CH₂CH₃ |
| O | H | F | CH₃ | 0 | 5-CH₃ | CO₂CH₂CH₃ |
| S | F | F | CH₃ | 0 | 5-CH₃ | CO₂CH₂CH₃ |
| O | F | F | CH₃ | 0 | 5-CH₃ | CO₂CH₂CH₃ |
| S | H | Cl | CH₃ | 0 | 5-CH₃ | CO₂CH₂CH₃ |
| O | H | Cl | CH₃ | 0 | 5-CH₃ | CO₂CH₂CH₃ |
| S | F | Cl | CH₃ | 0 | 5-CH₃ | CO₂CH₂CH₃ |
| O | F | Cl | CH₃ | 0 | 5-CH₃ | CO₂CH₂CH₃ |
| S | H | F | H | 0 | 5-CH₃ | CO₂(CH₂)₂CH₃ |
| O | H | F | H | 0 | 5-CH₃ | CO₂(CH₂)₂CH₃ |
| S | F | F | H | 0 | 5-CH₃ | CO₂(CH₂)₂CH₃ |
| O | F | F | H | 0 | 5-CH₃ | CO₂(CH₂)₂CH₃ |
| S | H | Cl | H | 0 | 5-CH₃ | CO₂(CH₂)₂CH₃ |
| O | H | Cl | H | 0 | 5-CH₃ | CO₂(CH₂)₂CH₃ |
| S | F | Cl | H | 0 | 5-CH₃ | CO₂(CH₂)₂CH₃ |
| O | F | Cl | H | 0 | 5-CH₃ | CO₂(CH₂)₂CH₃ |
| S | H | F | CH₃ | 0 | 5-CH₃ | CO₂(CH₂)₂CH₃ |
| O | H | F | CH₃ | 0 | 5-CH₃ | CO₂(CH₂)₂CH₃ |
| S | F | F | CH₃ | 0 | 5-CH₃ | CO₂(CH₂)₂CH₃ |
| O | F | F | CH₃ | 0 | 5-CH₃ | CO₂(CH₂)₂CH₃ |
| S | H | Cl | CH₃ | 0 | 5-CH₃ | CO₂(CH₂)₂CH₃ |
| O | H | Cl | CH₃ | 0 | 5-CH₃ | CO₂(CH₂)₂CH₃ |
| S | F | Cl | CH₃ | 0 | 5-CH₃ | CO₂(CH₂)₂CH₃ |
| O | F | Cl | CH₃ | 0 | 5-CH₃ | CO₂(CH₂)₂CH₃ |
| S | H | F | H | 0 | 5-CH₃ | CO₂CH(CH₃)₂ |
| O | H | F | H | 0 | 5-CH₃ | CO₂CH(CH₃)₂ |

TABLE 1-continued

| X | R¹ | R² | R³ | m | R⁵ | R⁴ |
|---|----|----|----|---|-----|-----|
| S | F | F | H | 0 | 5-$CH_3$ | $CO_2CH(CH_3)_2$ |
| O | F | F | H | 0 | 5-$CH_3$ | $CO_2CH(CH_3)_2$ |
| S | H | Cl | H | 0 | 5-$CH_3$ | $CO_2CH(CH_3)_2$ |
| O | H | Cl | H | 0 | 5-$CH_3$ | $CO_2CH(CH_3)_2$ |
| S | F | Cl | H | 0 | 5-$CH_3$ | $CO_2CH(CH_3)_2$ |
| O | F | Cl | H | 0 | 5-$CH_3$ | $CO_2CH(CH_3)_2$ |
| S | H | F | $CH_3$ | 0 | 5-$CH_3$ | $CO_2CH(CH_3)_2$ |
| O | H | F | $CH_3$ | 0 | 5-$CH_3$ | $CO_2CH(CH_3)_2$ |
| S | F | F | $CH_3$ | 0 | 5-$CH_3$ | $CO_2CH(CH_3)_2$ |
| O | F | F | $CH_3$ | 0 | 5-$CH_3$ | $CO_2CH(CH_3)_2$ |
| S | H | Cl | $CH_3$ | 0 | 5-$CH_3$ | $CO_2CH(CH_3)_2$ |
| O | H | Cl | $CH_3$ | 0 | 5-$CH_3$ | $CO_2CH(CH_3)_2$ |
| S | F | Cl | $CH_3$ | 0 | 5-$CH_3$ | $CO_2CH(CH_3)_2$ |
| O | F | Cl | $CH_3$ | 0 | 5-$CH_3$ | $CO_2CH(CH_3)_2$ |
| S | H | F | H | 0 | 5-$CH_3$ | $CO_2(CH_2)_3CH_3$ |
| O | H | F | H | 0 | 5-$CH_3$ | $CO_2(CH_2)_3CH_3$ |
| S | F | F | H | 0 | 5-$CH_3$ | $CO_2(CH_2)_3CH_3$ |
| O | F | F | H | 0 | 5-$CH_3$ | $CO_2(CH_2)_3CH_3$ |
| S | H | Cl | H | 0 | 5-$CH_3$ | $CO_2(CH_2)_3CH_3$ |
| O | H | Cl | H | 0 | 5-$CH_3$ | $CO_2(CH_2)_3CH_3$ |
| S | F | Cl | H | 0 | 5-$CH_3$ | $CO_2(CH_2)_3CH_3$ |
| O | F | Cl | H | 0 | 5-$CH_3$ | $CO_2(CH_2)_3CH_3$ |
| S | H | F | $CH_3$ | 0 | 5-$CH_3$ | $CO_2(CH_2)_3CH_3$ |
| O | H | F | $CH_3$ | 0 | 5-$CH_3$ | $CO_2(CH_2)_3CH_3$ |
| S | F | F | $CH_3$ | 0 | 5-$CH_3$ | $CO_2(CH_2)_3CH_3$ |
| O | F | F | $CH_3$ | 0 | 5-$CH_3$ | $CO_2(CH_2)_3CH_3$ |
| S | H | Cl | $CH_3$ | 0 | 5-$CH_3$ | $CO_2(CH_2)_3CH_3$ |
| O | H | Cl | $CH_3$ | 0 | 5-$CH_3$ | $CO_2(CH_2)_3CH_3$ |
| S | F | Cl | $CH_3$ | 0 | 5-$CH_3$ | $CO_2(CH_2)_3CH_3$ |
| O | F | Cl | $CH_3$ | 0 | 5-$CH_3$ | $CO_2(CH_2)_3CH_3$ |
| S | H | F | H | 0 | 5-$CH_3$ | $CO_2(CH_2)_2OCH_3$ |
| O | H | F | H | 0 | 5-$CH_3$ | $CO_2(CH_2)_2OCH_3$ |
| S | F | F | H | 0 | 5-$CH_3$ | $CO_2(CH_2)_2OCH_3$ |
| O | F | F | H | 0 | 5-$CH_3$ | $CO_2(CH_2)_2OCH_3$ |
| S | H | Cl | H | 0 | 5-$CH_3$ | $CO_2(CH_2)_2OCH_3$ |
| O | H | Cl | H | 0 | 5-$CH_3$ | $CO_2(CH_2)_2OCH_3$ |
| S | F | Cl | H | 0 | 5-$CH_3$ | $CO_2(CH_2)_2OCH_3$ |
| O | F | Cl | H | 0 | 5-$CH_3$ | $CO_2(CH_2)_2OCH_3$ |
| S | H | F | $CH_3$ | 0 | 5-$CH_3$ | $CO_2(CH_2)_2OCH_3$ |
| O | H | F | $CH_3$ | 0 | 5-$CH_3$ | $CO_2(CH_2)_2OCH_3$ |
| S | F | F | $CH_3$ | 0 | 5-$CH_3$ | $CO_2(CH_2)_2OCH_3$ |
| O | F | F | $CH_3$ | 0 | 5-$CH_3$ | $CO_2(CH_2)_2OCH_3$ |
| S | H | Cl | $CH_3$ | 0 | 5-$CH_3$ | $CO_2(CH_2)_2OCH_3$ |
| O | H | Cl | $CH_3$ | 0 | 5-$CH_3$ | $CO_2(CH_2)_2OCH_3$ |
| S | F | Cl | $CH_3$ | 0 | 5-$CH_3$ | $CO_2(CH_2)_2OCH_3$ |
| O | F | Cl | $CH_3$ | 0 | 5-$CH_3$ | $CO_2(CH_2)_2OCH_3$ |
| S | H | F | H | 0 | 5-$CH_3$ | $CO_2(CH_2)_2OCH_2CH_3$ |
| O | H | F | H | 0 | 5-$CH_3$ | $CO_2(CH_2)_2OCH_2CH_3$ |
| S | F | F | H | 0 | 5-$CH_3$ | $CO_2(CH_2)_2OCH_2CH_3$ |
| O | F | F | H | 0 | 5-$CH_3$ | $CO_2(CH_2)_2OCH_2CH_3$ |
| S | H | Cl | H | 0 | 5-$CH_3$ | $CO_2(CH_2)_2OCH_2CH_3$ |
| O | H | Cl | H | 0 | 5-$CH_3$ | $CO_2(CH_2)_2OCH_2CH_3$ |
| S | F | Cl | H | 0 | 5-$CH_3$ | $CO_2(CH_2)_2OCH_2CH_3$ |
| O | F | Cl | H | 0 | 5-$CH_3$ | $CO_2(CH_2)_2OCH_2CH_3$ |
| S | H | F | $CH_3$ | 0 | 5-$CH_3$ | $CO_2(CH_2)_2OCH_2CH_3$ |
| O | H | F | $CH_3$ | 0 | 5-$CH_3$ | $CO_2(CH_2)_2OCH_2CH_3$ |
| S | F | F | $CH_3$ | 0 | 5-$CH_3$ | $CO_2(CH_2)_2OCH_2CH_3$ |
| O | F | F | $CH_3$ | 0 | 5-$CH_3$ | $CO_2(CH_2)_2OCH_2CH_3$ |
| S | H | Cl | $CH_3$ | 0 | 5-$CH_3$ | $CO_2(CH_2)_2OCH_2CH_3$ |
| O | H | Cl | $CH_3$ | 0 | 5-$CH_3$ | $CO_2(CH_2)_2OCH_2CH_3$ |
| S | F | Cl | $CH_3$ | 0 | 5-$CH_3$ | $CO_2(CH_2)_2OCH_2CH_3$ |
| O | F | Cl | $CH_3$ | 0 | 5-$CH_3$ | $CO_2(CH_2)_2OCH_2CH_3$ |
| S | H | F | H | 0 | 4,5-Di-$CH_3$ | $CO_2CH_3$ |
| O | H | F | H | 0 | 4,5-Di-$CH_3$ | $CO_2CH_3$ |
| S | F | F | H | 0 | 4,5-Di-$CH_3$ | $CO_2CH_3$ |
| O | F | F | H | 0 | 4,5-Di-$CH_3$ | $CO_2CH_3$ |
| S | H | Cl | H | 0 | 4,5-Di-$CH_3$ | $CO_2CH_3$ |
| O | H | Cl | H | 0 | 4,5-Di-$CH_3$ | $CO_2CH_3$ |
| S | F | Cl | H | 0 | 4,5-Di-$CH_3$ | $CO_2CH_3$ |
| O | F | Cl | H | 0 | 4,5-Di-$CH_3$ | $CO_2CH_3$ |
| S | H | F | $CH_3$ | 0 | 4,5-Di-$CH_3$ | $CO_2CH_3$ |
| O | H | F | $CH_3$ | 0 | 4,5-Di-$CH_3$ | $CO_2CH_3$ |
| S | F | F | $CH_3$ | 0 | 4,5-Di-$CH_3$ | $CO_2CH_3$ |
| O | F | F | $CH_3$ | 0 | 4,5-Di-$CH_3$ | $CO_2CH_3$ |
| S | H | Cl | $CH_3$ | 0 | 4,5-Di-$CH_3$ | $CO_2CH_3$ |
| O | H | Cl | $CH_3$ | 0 | 4,5-Di-$CH_3$ | $CO_2CH_3$ |
| S | F | Cl | $CH_3$ | 0 | 4,5-Di-$CH_3$ | $CO_2CH_3$ |
| O | F | Cl | $CH_3$ | 0 | 4,5-Di-$CH_3$ | $CO_2CH_3$ |
| S | H | F | H | 0 | 4,5-Di-$CH_3$ | $CO_2CH_2CH_3$ |
| O | H | F | H | 0 | 4,5-Di-$CH_3$ | $CO_2CH_2CH_3$ |
| S | F | F | H | 0 | 4,5-Di-$CH_3$ | $CO_2CH_2CH_3$ |

TABLE 1-continued

| X | R¹ | R² | R³ | m | R⁵ | R⁴ |
|---|----|----|----|---|-----|-----|
| O | F | F | H | 0 | 4,5-Di-CH₃ | CO₂CH₂CH₃ |
| S | H | Cl | H | 0 | 4,5-Di-CH₃ | CO₂CH₂CH₃ |
| O | H | Cl | H | 0 | 4,5-Di-CH₃ | CO₂CH₂CH₃ |
| S | F | Cl | H | 0 | 4,5-Di-CH₃ | CO₂CH₂CH₃ |
| O | F | Cl | H | 0 | 4,5-Di-CH₃ | CO₂CH₂CH₃ |
| S | H | F | CH₃ | 0 | 4,5-Di-CH₃ | CO₂CH₂CH₃ |
| O | H | F | CH₃ | 0 | 4,5-Di-CH₃ | CO₂CH₂CH₃ |
| S | F | F | CH₃ | 0 | 4,5-Di-CH₃ | CO₂CH₂CH₃ |
| O | F | F | CH₃ | 0 | 4,5-Di-CH₃ | CO₂CH₂CH₃ |
| S | H | Cl | CH₃ | 0 | 4,5-Di-CH₃ | CO₂CH₂CH₃ |
| O | H | Cl | CH₃ | 0 | 4,5-Di-CH₃ | CO₂CH₂CH₃ |
| S | F | Cl | CH₃ | 0 | 4,5-Di-CH₃ | CO₂CH₂CH₃ |
| O | F | Cl | CH₃ | 0 | 4,5-Di-CH₃ | CO₂CH₂CH₃ |
| S | H | F | H | 0 | 4,5-Di-CH₃ | CO₂(CH₂)₂CH₃ |
| O | H | F | H | 0 | 4,5-Di-CH₃ | CO₂(CH₂)₂CH₃ |
| S | F | F | H | 0 | 4,5-Di-CH₃ | CO₂(CH₂)₂CH₃ |
| O | F | F | H | 0 | 4,5-Di-CH₃ | CO₂(CH₂)₂CH₃ |
| S | H | Cl | H | 0 | 4,5-Di-CH₃ | CO₂(CH₂)₂CH₃ |
| O | H | Cl | H | 0 | 4,5-Di-CH₃ | CO₂(CH₂)₂CH₃ |
| S | F | Cl | H | 0 | 4,5-Di-CH₃ | CO₂(CH₂)₂CH₃ |
| O | F | Cl | H | 0 | 4,5-Di-CH₃ | CO₂(CH₂)₂CH₃ |
| S | H | F | CH₃ | 0 | 4,5-Di-CH₃ | CO₂(CH₂)₂CH₃ |
| O | H | F | CH₃ | 0 | 4,5-Di-CH₃ | CO₂(CH₂)₂CH₃ |
| S | F | F | CH₃ | 0 | 4,5-Di-CH₃ | CO₂(CH₂)₂CH₃ |
| O | F | F | CH₃ | 0 | 4,5-Di-CH₃ | CO₂(CH₂)₂CH₃ |
| S | H | Cl | CH₃ | 0 | 4,5-Di-CH₃ | CO₂(CH₂)₂CH₃ |
| O | H | Cl | CH₃ | 0 | 4,5-Di-CH₃ | CO₂(CH₂)₂CH₃ |
| S | F | Cl | CH₃ | 0 | 4,5-Di-CH₃ | CO₂(CH₂)₂CH₃ |
| O | F | Cl | CH₃ | 0 | 4,5-Di-CH₃ | CO₂(CH₂)₂CH₃ |
| S | H | F | H | 0 | 4,5-Di-CH₃ | CO₂CH(CH₃)₂ |
| O | H | F | H | 0 | 4,5-Di-CH₃ | CO₂CH(CH₃)₂ |
| S | F | F | H | 0 | 4,5-Di-CH₃ | CO₂CH(CH₃)₂ |
| O | F | F | H | 0 | 4,5-Di-CH₃ | CO₂CH(CH₃)₂ |
| S | H | Cl | H | 0 | 4,5-Di-CH₃ | CO₂CH(CH₃)₂ |
| O | H | Cl | H | 0 | 4,5-Di-CH₃ | CO₂CH(CH₃)₂ |
| S | F | Cl | H | 0 | 4,5-Di-CH₃ | CO₂CH(CH₃)₂ |
| O | F | Cl | H | 0 | 4,5-Di-CH₃ | CO₂CH(CH₃)₂ |
| S | H | F | CH₃ | 0 | 4,5-Di-CH₃ | CO₂CH(CH₃)₂ |
| O | H | F | CH₃ | 0 | 4,5-Di-CH₃ | CO₂CH(CH₃)₂ |
| S | F | F | CH₃ | 0 | 4,5-Di-CH₃ | CO₂CH(CH₃)₂ |
| O | F | F | CH₃ | 0 | 4,5-Di-CH₃ | CO₂CH(CH₃)₂ |
| S | H | Cl | CH₃ | 0 | 4,5-Di-CH₃ | CO₂CH(CH₃)₂ |
| O | H | Cl | CH₃ | 0 | 4,5-Di-CH₃ | CO₂CH(CH₃)₂ |
| S | F | Cl | CH₃ | 0 | 4,5-Di-CH₃ | CO₂CH(CH₃)₂ |
| O | F | Cl | CH₃ | 0 | 4,5-Di-CH₃ | CO₂CH(CH₃)₂ |
| S | H | F | H | 0 | 4,5-Di-CH₃ | CO₂(CH₂)₃CH₃ |
| O | H | F | H | 0 | 4,5-Di-CH₃ | CO₂(CH₂)₃CH₃ |
| S | F | F | H | 0 | 4,5-Di-CH₃ | CO₂(CH₂)₃CH₃ |
| O | F | F | H | 0 | 4,5-Di-CH₃ | CO₂(CH₂)₃CH₃ |
| S | H | Cl | H | 0 | 4,5-Di-CH₃ | CO₂(CH₂)₃CH₃ |
| O | H | Cl | H | 0 | 4,5-Di-CH₃ | CO₂(CH₂)₃CH₃ |
| S | F | Cl | H | 0 | 4,5-Di-CH₃ | CO₂(CH₂)₃CH₃ |
| O | F | Cl | H | 0 | 4,5-Di-CH₃ | CO₂(CH₂)₃CH₃ |
| S | H | F | CH₃ | 0 | 4,5-Di-CH₃ | CO₂(CH₂)₃CH₃ |
| O | H | F | CH₃ | 0 | 4,5-Di-CH₃ | CO₂(CH₂)₃CH₃ |
| S | F | F | CH₃ | 0 | 4,5-Di-CH₃ | CO₂(CH₂)₃CH₃ |
| O | F | F | CH₃ | 0 | 4,5-Di-CH₃ | CO₂(CH₂)₃CH₃ |
| S | H | Cl | CH₃ | 0 | 4,5-Di-CH₃ | CO₂(CH₂)₃CH₃ |
| O | H | Cl | CH₃ | 0 | 4,5-Di-CH₃ | CO₂(CH₂)₃CH₃ |
| S | F | Cl | CH₃ | 0 | 4,5-Di-CH₃ | CO₂(CH₂)₃CH₃ |
| O | F | Cl | CH₃ | 0 | 4,5-Di-CH₃ | CO₂(CH₂)₃CH₃ |
| S | H | F | H | 0 | 4,5-Di-CH₃ | CO₂(CH₂)₂OCH₃ |
| O | H | F | H | 0 | 4,5-Di-CH₃ | CO₂(CH₂)₂OCH₃ |
| S | F | F | H | 0 | 4,5-Di-CH₃ | CO₂(CH₂)₂OCH₃ |
| O | F | F | H | 0 | 4,5-Di-CH₃ | CO₂(CH₂)₂OCH₃ |
| S | H | Cl | H | 0 | 4,5-Di-CH₃ | CO₂(CH₂)₂OCH₃ |
| O | H | Cl | H | 0 | 4,5-Di-CH₃ | CO₂(CH₂)₂OCH₃ |
| S | F | Cl | H | 0 | 4,5-Di-CH₃ | CO₂(CH₂)₂OCH₃ |
| O | F | Cl | H | 0 | 4,5-Di-CH₃ | CO₂(CH₂)₂OCH₃ |
| S | H | F | CH₃ | 0 | 4,5-Di-CH₃ | CO₂(CH₂)₂OCH₃ |
| O | H | F | CH₃ | 0 | 4,5-Di-CH₃ | CO₂(CH₂)₂OCH₃ |
| S | F | F | CH₃ | 0 | 4,5-Di-CH₃ | CO₂(CH₂)₂OCH₃ |
| O | F | F | CH₃ | 0 | 4,5-Di-CH₃ | CO₂(CH₂)₂OCH₃ |
| S | H | Cl | CH₃ | 0 | 4,5-Di-CH₃ | CO₂(CH₂)₂OCH₃ |
| O | H | Cl | CH₃ | 0 | 4,5-Di-CH₃ | CO₂(CH₂)₂OCH₃ |
| S | F | Cl | CH₃ | 0 | 4,5-Di-CH₃ | CO₂(CH₂)₂OCH₃ |
| O | F | Cl | CH₃ | 0 | 4,5-Di-CH₃ | CO₂(CH₂)₂OCH₃ |
| S | H | F | H | 0 | 4,5-Di-CH₃ | CO₂(CH₂)₂OCH₂CH₃ |
| O | H | F | H | 0 | 4,5-Di-CH₃ | CO₂(CH₂)₂OCH₂CH₃ |
| S | F | F | H | 0 | 4,5-Di-CH₃ | CO₂(CH₂)₂OCH₂CH₃ |
| O | F | F | H | 0 | 4,5-Di-CH₃ | CO₂(CH₂)₂OCH₂CH₃ |

TABLE 1-continued

| X | R$^1$ | R$^2$ | R$^3$ | m | R$^5$ | R$^4$ |
|---|---|---|---|---|---|---|
| S | H | Cl | H | 0 | 4,5-Di-CH$_3$ | CO$_2$(CH$_2$)$_2$OCH$_2$CH$_3$ |
| O | H | Cl | H | 0 | 4,5-Di-CH$_3$ | CO$_2$(CH$_2$)$_2$OCH$_2$CH$_3$ |
| S | F | Cl | H | 0 | 4,5-Di-CH$_3$ | CO$_2$(CH$_2$)$_2$OCH$_2$CH$_3$ |
| O | F | Cl | H | 0 | 4,5-Di-CH$_3$ | CO$_2$(CH$_2$)$_2$OCH$_2$CH$_3$ |
| S | H | F | CH$_3$ | 0 | 4,5-Di-CH$_3$ | CO$_2$(CH$_2$)$_2$OCH$_2$CH$_3$ |
| O | H | F | CH$_3$ | 0 | 4,5-Di-CH$_3$ | CO$_2$(CH$_2$)$_2$OCH$_2$CH$_3$ |
| S | F | F | CH$_3$ | 0 | 4,5-Di-CH$_3$ | CO$_2$(CH$_2$)$_2$OCH$_2$CH$_3$ |
| O | F | F | CH$_3$ | 0 | 4,5-Di-CH$_3$ | CO$_2$(CH$_2$)$_2$OCH$_2$CH$_3$ |
| S | H | Cl | CH$_3$ | 0 | 4,5-Di-CH$_3$ | CO$_2$(CH$_2$)$_2$OCH$_2$CH$_3$ |
| O | H | Cl | CH$_3$ | 0 | 4,5-Di-CH$_3$ | CO$_2$(CH$_2$)$_2$OCH$_2$CH$_3$ |
| S | F | Cl | CH$_3$ | 0 | 4,5-Di-CH$_3$ | CO$_2$(CH$_2$)$_2$OCH$_2$CH$_3$ |
| O | F | Cl | CH$_3$ | 0 | 4,5-Di-CH$_3$ | CO$_2$(CH$_2$)$_2$OCH$_2$CH$_3$ |
| S | H | F | H | 1 | H | CO$_2$CH$_3$ |
| O | H | F | H | 1 | H | CO$_2$CH$_3$ |
| S | F | F | H | 1 | H | CO$_2$CH$_3$ |
| O | F | F | H | 1 | H | CO$_2$CH$_3$ |
| S | H | Cl | H | 1 | H | CO$_2$CH$_3$ |
| O | H | Cl | H | 1 | H | CO$_2$CH$_3$ |
| S | F | Cl | H | 1 | H | CO$_2$CH$_3$ |
| O | F | Cl | H | 1 | H | CO$_2$CH$_3$ |
| S | H | F | CH$_3$ | 1 | H | CO$_2$CH$_3$ |
| O | H | F | CH$_3$ | 1 | H | CO$_2$CH$_3$ |
| S | F | F | CH$_3$ | 1 | H | CO$_2$CH$_3$ |
| O | F | F | CH$_3$ | 1 | H | CO$_2$CH$_3$ |
| S | H | Cl | CH$_3$ | 1 | H | CO$_2$CH$_3$ |
| O | H | Cl | CH$_3$ | 1 | H | CO$_2$CH$_3$ |
| S | F | Cl | CH$_3$ | 1 | H | CO$_2$CH$_3$ |
| O | F | Cl | CH$_3$ | 1 | H | CO$_2$CH$_3$ |
| S | H | F | H | 1 | H | CO$_2$CH$_2$CH$_3$ |
| O | H | F | H | 1 | H | CO$_2$CH$_2$CH$_3$ |
| S | F | F | H | 1 | H | CO$_2$CH$_2$CH$_3$ |
| O | F | F | H | 1 | H | CO$_2$CH$_2$CH$_3$ |
| S | H | Cl | H | 1 | H | CO$_2$CH$_2$CH$_3$ |
| O | H | Cl | H | 1 | H | CO$_2$CH$_2$CH$_3$ |
| S | F | Cl | H | 1 | H | CO$_2$CH$_2$CH$_3$ |
| O | F | Cl | H | 1 | H | CO$_2$CH$_2$CH$_3$ |
| S | H | F | CH$_3$ | 1 | H | CO$_2$CH$_2$CH$_3$ |
| O | H | F | CH$_3$ | 1 | H | CO$_2$CH$_2$CH$_3$ |
| S | F | F | CH$_3$ | 1 | H | CO$_2$CH$_2$CH$_3$ |
| O | F | F | CH$_3$ | 1 | H | CO$_2$CH$_2$CH$_3$ |
| S | H | Cl | CH$_3$ | 1 | H | CO$_2$CH$_2$CH$_3$ |
| O | H | Cl | CH$_3$ | 1 | H | CO$_2$CH$_2$CH$_3$ |
| S | F | Cl | CH$_3$ | 1 | H | CO$_2$CH$_2$CH$_3$ |
| O | F | Cl | CH$_3$ | 1 | H | CO$_2$CH$_2$CH$_3$ |
| S | H | F | H | 1 | H | CO$_2$(CH$_2$)$_2$CH$_3$ |
| O | H | F | H | 1 | H | CO$_2$(CH$_2$)$_2$CH$_3$ |
| S | F | F | H | 1 | H | CO$_2$(CH$_2$)$_2$CH$_3$ |
| O | F | F | H | 1 | H | CO$_2$(CH$_2$)$_2$CH$_3$ |
| S | H | Cl | H | 1 | H | CO$_2$(CH$_2$)$_2$CH$_3$ |
| O | H | Cl | H | 1 | H | CO$_2$(CH$_2$)$_2$CH$_3$ |
| S | F | Cl | H | 1 | H | CO$_2$(CH$_2$)$_2$CH$_3$ |
| O | F | Cl | H | 1 | H | CO$_2$(CH$_2$)$_2$CH$_3$ |
| S | H | F | CH$_3$ | 1 | H | CO$_2$(CH$_2$)$_2$CH$_3$ |
| O | H | F | CH$_3$ | 1 | H | CO$_2$(CH$_2$)$_2$CH$_3$ |
| S | F | F | CH$_3$ | 1 | H | CO$_2$(CH$_2$)$_2$CH$_3$ |
| O | F | F | CH$_3$ | 1 | H | CO$_2$(CH$_2$)$_2$CH$_3$ |
| S | H | Cl | CH$_3$ | 1 | H | CO$_2$(CH$_2$)$_2$CH$_3$ |
| O | H | Cl | CH$_3$ | 1 | H | CO$_2$(CH$_2$)$_2$CH$_3$ |
| S | F | Cl | CH$_3$ | 1 | H | CO$_2$(CH$_2$)$_2$CH$_3$ |
| O | F | Cl | CH$_3$ | 1 | H | CO$_2$(CH$_2$)$_2$CH$_3$ |
| S | H | F | H | 1 | H | CO$_2$CH(CH$_3$)$_2$ |
| O | H | F | H | 1 | H | CO$_2$CH(CH$_3$)$_2$ |
| S | F | F | H | 1 | H | CO$_2$CH(CH$_3$)$_2$ |
| O | F | F | H | 1 | H | CO$_2$CH(CH$_3$)$_2$ |
| S | H | Cl | H | 1 | H | CO$_2$CH(CH$_3$)$_2$ |
| O | H | Cl | H | 1 | H | CO$_2$CH(CH$_3$)$_2$ |
| S | F | Cl | H | 1 | H | CO$_2$CH(CH$_3$)$_2$ |
| O | F | Cl | H | 1 | H | CO$_2$CH(CH$_3$)$_2$ |
| S | H | F | CH$_3$ | 1 | H | CO$_2$CH(CH$_3$)$_2$ |
| O | H | F | CH$_3$ | 1 | H | CO$_2$CH(CH$_3$)$_2$ |
| S | F | F | CH$_3$ | 1 | H | CO$_2$CH(CH$_3$)$_2$ |
| O | F | F | CH$_3$ | 1 | H | CO$_2$CH(CH$_3$)$_2$ |
| S | H | Cl | CH$_3$ | 1 | H | CO$_2$CH(CH$_3$)$_2$ |
| O | H | Cl | CH$_3$ | 1 | H | CO$_2$CH(CH$_3$)$_2$ |
| S | F | Cl | CH$_3$ | 1 | H | CO$_2$CH(CH$_3$)$_2$ |
| O | F | Cl | CH$_3$ | 1 | H | CO$_2$CH(CH$_3$)$_2$ |
| S | H | F | H | 1 | H | CO$_2$(CH$_2$)$_3$CH$_3$ |
| O | H | F | H | 1 | H | CO$_2$(CH$_2$)$_3$CH$_3$ |
| S | F | F | H | 1 | H | CO$_2$(CH$_2$)$_3$CH$_3$ |
| O | F | F | H | 1 | H | CO$_2$(CH$_2$)$_3$CH$_3$ |
| S | H | Cl | H | 1 | H | CO$_2$(CH$_2$)$_3$CH$_3$ |

TABLE 1-continued

| X | R¹ | R² | R³ | m | R⁵ | R⁴ |
|---|---|---|---|---|---|---|
| O | H | Cl | H | 1 | H | $CO_2(CH_2)_3CH_3$ |
| S | F | Cl | H | 1 | H | $CO_2(CH_2)_3CH_3$ |
| O | F | Cl | H | 1 | H | $CO_2(CH_2)_3CH_3$ |
| S | H | F | $CH_3$ | 1 | H | $CO_2(CH_2)_3CH_3$ |
| O | H | F | $CH_3$ | 1 | H | $CO_2(CH_2)_3CH_3$ |
| S | F | F | $CH_3$ | 1 | H | $CO_2(CH_2)_3CH_3$ |
| O | F | F | $CH_3$ | 1 | H | $CO_2(CH_2)_3CH_3$ |
| S | H | Cl | $CH_3$ | 1 | H | $CO_2(CH_2)_3CH_3$ |
| O | H | Cl | $CH_3$ | 1 | H | $CO_2(CH_2)_3CH_3$ |
| S | F | Cl | $CH_3$ | 1 | H | $CO_2(CH_2)_3CH_3$ |
| O | F | Cl | $CH_3$ | 1 | H | $CO_2(CH_2)_3CH_3$ |
| S | H | F | H | 1 | H | $CO_2(CH_2)_2OCH_3$ |
| O | H | F | H | 1 | H | $CO_2(CH_2)_2OCH_3$ |
| S | F | F | H | 1 | H | $CO_2(CH_2)_2OCH_3$ |
| O | F | F | H | 1 | H | $CO_2(CH_2)_2OCH_3$ |
| S | H | Cl | H | 1 | H | $CO_2(CH_2)_2OCH_3$ |
| O | H | Cl | H | 1 | H | $CO_2(CH_2)_2OCH_3$ |
| S | F | Cl | H | 1 | H | $CO_2(CH_2)_2OCH_3$ |
| O | F | Cl | H | 1 | H | $CO_2(CH_2)_2OCH_3$ |
| S | H | F | $CH_3$ | 1 | H | $CO_2(CH_2)_2OCH_3$ |
| O | H | F | $CH_3$ | 1 | H | $CO_2(CH_2)_2OCH_3$ |
| S | F | F | $CH_3$ | 1 | H | $CO_2(CH_2)_2OCH_3$ |
| O | F | F | $CH_3$ | 1 | H | $CO_2(CH_2)_2OCH_3$ |
| S | H | Cl | $CH_3$ | 1 | H | $CO_2(CH_2)_2OCH_3$ |
| O | H | Cl | $CH_3$ | 1 | H | $CO_2(CH_2)_2OCH_3$ |
| S | F | Cl | $CH_3$ | 1 | H | $CO_2(CH_2)_2OCH_3$ |
| O | F | Cl | $CH_3$ | 1 | H | $CO_2(CH_2)_2OCH_3$ |
| S | H | F | H | 1 | H | $CO_2(CH_2)_2OCH_2CH_3$ |
| O | H | F | H | 1 | H | $CO_2(CH_2)_2OCH_2CH_3$ |
| S | F | F | H | 1 | H | $CO_2(CH_2)_2OCH_2CH_3$ |
| O | F | F | H | 1 | H | $CO_2(CH_2)_2OCH_2CH_3$ |
| S | H | Cl | H | 1 | H | $CO_2(CH_2)_2OCH_2CH_3$ |
| O | H | Cl | H | 1 | H | $CO_2(CH_2)_2OCH_2CH_3$ |
| S | F | Cl | H | 1 | H | $CO_2(CH_2)_2OCH_2CH_3$ |
| O | F | Cl | H | 1 | H | $CO_2(CH_2)_2OCH_2CH_3$ |
| S | H | F | $CH_3$ | 1 | H | $CO_2(CH_2)_2OCH_2CH_3$ |
| O | H | F | $CH_3$ | 1 | H | $CO_2(CH_2)_2OCH_2CH_3$ |
| S | F | F | $CH_3$ | 1 | H | $CO_2(CH_2)_2OCH_2CH_3$ |
| O | F | F | $CH_3$ | 1 | H | $CO_2(CH_2)_2OCH_2CH_3$ |
| S | H | Cl | $CH_3$ | 1 | H | $CO_2(CH_2)_2OCH_2CH_3$ |
| O | H | Cl | $CH_3$ | 1 | H | $CO_2(CH_2)_2OCH_2CH_3$ |
| S | F | Cl | $CH_3$ | 1 | H | $CO_2(CH_2)_2OCH_2CH_3$ |
| O | F | Cl | $CH_3$ | 1 | H | $CO_2(CH_2)_2OCH_2CH_3$ |
| S | H | F | H | 1 | 4-$CH_3$ | $CO_2CH_3$ |
| O | H | F | H | 1 | 4-$CH_3$ | $CO_2CH_3$ |
| S | F | F | H | 1 | 4-$CH_3$ | $CO_2CH_3$ |
| O | F | F | H | 1 | 4-$CH_3$ | $CO_2CH_3$ |
| S | H | Cl | H | 1 | 4-$CH_3$ | $CO_2CH_3$ |
| O | H | Cl | H | 1 | 4-$CH_3$ | $CO_2CH_3$ |
| S | F | Cl | H | 1 | 4-$CH_3$ | $CO_2CH_3$ |
| O | F | Cl | H | 1 | 4-$CH_3$ | $CO_2CH_3$ |
| S | H | F | $CH_3$ | 1 | 4-$CH_3$ | $CO_2CH_3$ |
| O | H | F | $CH_3$ | 1 | 4-$CH_3$ | $CO_2CH_3$ |
| S | F | F | $CH_3$ | 1 | 4-$CH_3$ | $CO_2CH_3$ |
| O | F | F | $CH_3$ | 1 | 4-$CH_3$ | $CO_2CH_3$ |
| S | H | Cl | $CH_3$ | 1 | 4-$CH_3$ | $CO_2CH_3$ |
| O | H | Cl | $CH_3$ | 1 | 4-$CH_3$ | $CO_2CH_3$ |
| S | F | Cl | $CH_3$ | 1 | 4-$CH_3$ | $CO_2CH_3$ |
| O | F | Cl | $CH_3$ | 1 | 4-$CH_3$ | $CO_2CH_3$ |
| S | H | F | H | 1 | 4-$CH_3$ | $CO_2CH_2CH_3$ |
| O | H | F | H | 1 | 4-$CH_3$ | $CO_2CH_2CH_3$ |
| S | F | F | H | 1 | 4-$CH_3$ | $CO_2CH_2CH_3$ |
| O | F | F | H | 1 | 4-$CH_3$ | $CO_2CH_2CH_3$ |
| S | H | Cl | H | 1 | 4-$CH_3$ | $CO_2CH_2CH_3$ |
| O | H | Cl | H | 1 | 4-$CH_3$ | $CO_2CH_2CH_3$ |
| S | F | Cl | H | 1 | 4-$CH_3$ | $CO_2CH_2CH_3$ |
| O | F | Cl | H | 1 | 4-$CH_3$ | $CO_2CH_2CH_3$ |
| S | H | F | $CH_3$ | 1 | 4-$CH_3$ | $CO_2CH_2CH_3$ |
| O | H | F | $CH_3$ | 1 | 4-$CH_3$ | $CO_2CH_2CH_3$ |
| S | F | F | $CH_3$ | 1 | 4-$CH_3$ | $CO_2CH_2CH_3$ |
| O | F | F | $CH_3$ | 1 | 4-$CH_3$ | $CO_2CH_2CH_3$ |
| S | H | Cl | $CH_3$ | 1 | 4-$CH_3$ | $CO_2CH_2CH_3$ |
| O | H | Cl | $CH_3$ | 1 | 4-$CH_3$ | $CO_2CH_2CH_3$ |
| S | F | Cl | $CH_3$ | 1 | 4-$CH_3$ | $CO_2CH_2CH_3$ |
| O | F | Cl | $CH_3$ | 1 | 4-$CH_3$ | $CO_2CH_2CH_3$ |
| S | H | F | H | 1 | 4-$CH_3$ | $CO_2(CH_2)_2CH_3$ |
| O | H | F | H | 1 | 4-$CH_3$ | $CO_2(CH_2)_2CH_3$ |
| S | F | F | H | 1 | 4-$CH_3$ | $CO_2(CH_2)_2CH_3$ |
| O | F | F | H | 1 | 4-$CH_3$ | $CO_2(CH_2)_2CH_3$ |
| S | H | Cl | H | 1 | 4-$CH_3$ | $CO_2(CH_2)_2CH_3$ |
| O | H | Cl | H | 1 | 4-$CH_3$ | $CO_2(CH_2)_2CH_3$ |

TABLE 1-continued

| X | R¹ | R² | R³ | m | R⁵ | R⁴ |
|---|---|---|---|---|---|---|
| S | F | Cl | H | 1 | 4-CH₃ | CO₂(CH₂)₂CH₃ |
| O | F | Cl | H | 1 | 4-CH₃ | CO₂(CH₂)₂CH₃ |
| S | H | F | CH₃ | 1 | 4-CH₃ | CO₂(CH₂)₂CH₃ |
| O | H | F | CH₃ | 1 | 4-CH₃ | CO₂(CH₂)₂CH₃ |
| S | F | F | CH₃ | 1 | 4-CH₃ | CO₂(CH₂)₂CH₃ |
| O | F | F | CH₃ | 1 | 4-CH₃ | CO₂(CH₂)₂CH₃ |
| S | H | Cl | CH₃ | 1 | 4-CH₃ | CO₂(CH₂)₂CH₃ |
| O | H | Cl | CH₃ | 1 | 4-CH₃ | CO₂(CH₂)₂CH₃ |
| S | F | Cl | CH₃ | 1 | 4-CH₃ | CO₂(CH₂)₂CH₃ |
| O | F | Cl | CH₃ | 1 | 4-CH₃ | CO₂(CH₂)₂CH₃ |
| S | H | F | H | 1 | 4-CH₃ | CO₂CH(CH₃)₂ |
| O | H | F | H | 1 | 4-CH₃ | CO₂CH(CH₃)₂ |
| S | F | F | H | 1 | 4-CH₃ | CO₂CH(CH₃)₂ |
| O | F | F | H | 1 | 4-CH₃ | CO₂CH(CH₃)₂ |
| S | H | Cl | H | 1 | 4-CH₃ | CO₂CH(CH₃)₂ |
| O | H | Cl | H | 1 | 4-CH₃ | CO₂CH(CH₃)₂ |
| S | F | Cl | H | 1 | 4-CH₃ | CO₂CH(CH₃)₂ |
| O | F | Cl | H | 1 | 4-CH₃ | CO₂CH(CH₃)₂ |
| S | H | F | CH₃ | 1 | 4-CH₃ | CO₂CH(CH₃)₂ |
| O | H | F | CH₃ | 1 | 4-CH₃ | CO₂CH(CH₃)₂ |
| S | F | F | CH₃ | 1 | 4-CH₃ | CO₂CH(CH₃)₂ |
| O | F | F | CH₃ | 1 | 4-CH₃ | CO₂CH(CH₃)₂ |
| S | H | Cl | CH₃ | 1 | 4-CH₃ | CO₂CH(CH₃)₂ |
| O | H | Cl | CH₃ | 1 | 4-CH₃ | CO₂CH(CH₃)₂ |
| S | F | Cl | CH₃ | 1 | 4-CH₃ | CO₂CH(CH₃)₂ |
| O | F | Cl | CH₃ | 1 | 4-CH₃ | CO₂CH(CH₃)₂ |
| S | H | F | H | 1 | 4-CH₃ | CO₂(CH₂)₃CH₃ |
| O | H | F | H | 1 | 4-CH₃ | CO₂(CH₂)₃CH₃ |
| S | F | F | H | 1 | 4-CH₃ | CO₂(CH₂)₃CH₃ |
| O | F | F | H | 1 | 4-CH₃ | CO₂(CH₂)₃CH₃ |
| S | H | Cl | H | 1 | 4-CH₃ | CO₂(CH₂)₃CH₃ |
| O | H | Cl | H | 1 | 4-CH₃ | CO₂(CH₂)₃CH₃ |
| S | F | Cl | H | 1 | 4-CH₃ | CO₂(CH₂)₃CH₃ |
| O | F | Cl | H | 1 | 4-CH₃ | CO₂(CH₂)₃CH₃ |
| S | H | F | CH₃ | 1 | 4-CH₃ | CO₂(CH₂)₃CH₃ |
| O | H | F | CH₃ | 1 | 4-CH₃ | CO₂(CH₂)₃CH₃ |
| S | F | F | CH₃ | 1 | 4-CH₃ | CO₂(CH₂)₃CH₃ |
| O | F | F | CH₃ | 1 | 4-CH₃ | CO₂(CH₂)₃CH₃ |
| S | H | Cl | CH₃ | 1 | 4-CH₃ | CO₂(CH₂)₃CH₃ |
| O | H | Cl | CH₃ | 1 | 4-CH₃ | CO₂(CH₂)₃CH₃ |
| S | F | Cl | CH₃ | 1 | 4-CH₃ | CO₂(CH₂)₃CH₃ |
| O | F | Cl | CH₃ | 1 | 4-CH₃ | CO₂(CH₂)₃CH₃ |
| S | H | F | H | 1 | 4-CH₃ | CO₂(CH₂)₂OCH₃ |
| O | H | F | H | 1 | 4-CH₃ | CO₂(CH₂)₂OCH₃ |
| S | F | F | H | 1 | 4-CH₃ | CO₂(CH₂)₂OCH₃ |
| O | F | F | H | 1 | 4-CH₃ | CO₂(CH₂)₂OCH₃ |
| S | H | Cl | H | 1 | 4-CH₃ | CO₂(CH₂)₂OCH₃ |
| O | H | Cl | H | 1 | 4-CH₃ | CO₂(CH₂)₂OCH₃ |
| S | F | Cl | H | 1 | 4-CH₃ | CO₂(CH₂)₂OCH₃ |
| O | F | Cl | H | 1 | 4-CH₃ | CO₂(CH₂)₂OCH₃ |
| S | H | F | CH₃ | 1 | 4-CH₃ | CO₂(CH₂)₂OCH₃ |
| O | H | F | CH₃ | 1 | 4-CH₃ | CO₂(CH₂)₂OCH₃ |
| S | F | F | CH₃ | 1 | 4-CH₃ | CO₂(CH₂)₂OCH₃ |
| O | F | F | CH₃ | 1 | 4-CH₃ | CO₂(CH₂)₂OCH₃ |
| S | H | Cl | CH₃ | 1 | 4-CH₃ | CO₂(CH₂)₂OCH₃ |
| O | H | Cl | CH₃ | 1 | 4-CH₃ | CO₂(CH₂)₂OCH₃ |
| S | F | Cl | CH₃ | 1 | 4-CH₃ | CO₂(CH₂)₂OCH₃ |
| O | F | Cl | CH₃ | 1 | 4-CH₃ | CO₂(CH₂)₂OCH₃ |
| S | H | F | H | 1 | 4-CH₃ | CO₂(CH₂)₂OCH₂CH₃ |
| O | H | F | H | 1 | 4-CH₃ | CO₂(CH₂)₂OCH₂CH₃ |
| S | F | F | H | 1 | 4-CH₃ | CO₂(CH₂)₂OCH₂CH₃ |
| O | F | F | H | 1 | 4-CH₃ | CO₂(CH₂)₂OCH₂CH₃ |
| S | H | Cl | H | 1 | 4-CH₃ | CO₂(CH₂)₂OCH₂CH₃ |
| O | H | Cl | H | 1 | 4-CH₃ | CO₂(CH₂)₂OCH₂CH₃ |
| S | F | Cl | H | 1 | 4-CH₃ | CO₂(CH₂)₂OCH₂CH₃ |
| O | F | Cl | H | 1 | 4-CH₃ | CO₂(CH₂)₂OCH₂CH₃ |
| S | H | F | CH₃ | 1 | 4-CH₃ | CO₂(CH₂)₂OCH₂CH₃ |
| O | H | F | CH₃ | 1 | 4-CH₃ | CO₂(CH₂)₂OCH₂CH₃ |
| S | F | F | CH₃ | 1 | 4-CH₃ | CO₂(CH₂)₂OCH₂CH₃ |
| O | F | F | CH₃ | 1 | 4-CH₃ | CO₂(CH₂)₂OCH₂CH₃ |
| S | H | Cl | CH₃ | 1 | 4-CH₃ | CO₂(CH₂)₂OCH₂CH₃ |
| O | H | Cl | CH₃ | 1 | 4-CH₃ | CO₂(CH₂)₂OCH₂CH₃ |
| S | F | Cl | CH₃ | 1 | 4-CH₃ | CO₂(CH₂)₂OCH₂CH₃ |
| O | F | Cl | CH₃ | 1 | 4-CH₃ | CO₂(CH₂)₂OCH₂CH₃ |
| S | H | F | H | 1 | 6-CH₃ | CO₂CH₃ |
| O | H | F | H | 1 | 6-CH₃ | CO₂CH₃ |
| S | F | F | H | 1 | 6-CH₃ | CO₂CH₃ |
| O | F | F | H | 1 | 6-CH₃ | CO₂CH₃ |
| S | H | Cl | H | 1 | 6-CH₃ | CO₂CH₃ |
| O | H | Cl | H | 1 | 6-CH₃ | CO₂CH₃ |
| S | F | Cl | H | 1 | 6-CH₃ | CO₂CH₃ |

TABLE 1-continued

| X | R¹ | R² | R³ | m | R⁵ | R⁴ |
|---|----|----|----|---|----|----|
| O | F | Cl | H | 1 | 6-$CH_3$ | $CO_2CH_3$ |
| S | H | F | $CH_3$ | 1 | 6-$CH_3$ | $CO_2CH_3$ |
| O | H | F | $CH_3$ | 1 | 6-$CH_3$ | $CO_2CH_3$ |
| S | F | F | $CH_3$ | 1 | 6-$CH_3$ | $CO_2CH_3$ |
| O | F | F | $CH_3$ | 1 | 6-$CH_3$ | $CO_2CH_3$ |
| S | H | Cl | $CH_3$ | 1 | 6-$CH_3$ | $CO_2CH_3$ |
| O | H | Cl | $CH_3$ | 1 | 6-$CH_3$ | $CO_2CH_3$ |
| S | F | Cl | $CH_3$ | 1 | 6-$CH_3$ | $CO_2CH_3$ |
| O | F | Cl | $CH_3$ | 1 | 6-$CH_3$ | $CO_2CH_3$ |
| S | H | F | H | 1 | 6-$CH_3$ | $CO_2CH_2CH_3$ |
| O | H | F | H | 1 | 6-$CH_3$ | $CO_2CH_2CH_3$ |
| S | F | F | H | 1 | 6-$CH_3$ | $CO_2CH_2CH_3$ |
| O | F | F | H | 1 | 6-$CH_3$ | $CO_2CH_2CH_3$ |
| S | H | Cl | H | 1 | 6-$CH_3$ | $CO_2CH_2CH_3$ |
| O | H | Cl | H | 1 | 6-$CH_3$ | $CO_2CH_2CH_3$ |
| S | F | Cl | H | 1 | 6-$CH_3$ | $CO_2CH_2CH_3$ |
| O | F | Cl | H | 1 | 6-$CH_3$ | $CO_2CH_2CH_3$ |
| S | H | F | $CH_3$ | 1 | 6-$CH_3$ | $CO_2CH_2CH_3$ |
| O | H | F | $CH_3$ | 1 | 6-$CH_3$ | $CO_2CH_2CH_3$ |
| S | F | F | $CH_3$ | 1 | 6-$CH_3$ | $CO_2CH_2CH_3$ |
| O | F | F | $CH_3$ | 1 | 6-$CH_3$ | $CO_2CH_2CH_3$ |
| S | H | Cl | $CH_3$ | 1 | 6-$CH_3$ | $CO_2CH_2CH_3$ |
| O | H | Cl | $CH_3$ | 1 | 6-$CH_3$ | $CO_2CH_2CH_3$ |
| S | F | Cl | $CH_3$ | 1 | 6-$CH_3$ | $CO_2CH_2CH_3$ |
| O | F | Cl | $CH_3$ | 1 | 6-$CH_3$ | $CO_2CH_2CH_3$ |
| S | H | F | H | 1 | 6-$CH_3$ | $CO_2(CH_2)_2CH_3$ |
| O | H | F | H | 1 | 6-$CH_3$ | $CO_2(CH_2)_2CH_3$ |
| S | F | F | H | 1 | 6-$CH_3$ | $CO_2(CH_2)_2CH_3$ |
| O | F | F | H | 1 | 6-$CH_3$ | $CO_2(CH_2)_2CH_3$ |
| S | H | Cl | H | 1 | 6-$CH_3$ | $CO_2(CH_2)_2CH_3$ |
| O | H | Cl | H | 1 | 6-$CH_3$ | $CO_2(CH_2)_2CH_3$ |
| S | F | Cl | H | 1 | 6-$CH_3$ | $CO_2(CH_2)_2CH_3$ |
| O | F | Cl | H | 1 | 6-$CH_3$ | $CO_2(CH_2)_2CH_3$ |
| S | H | F | $CH_3$ | 1 | 6-$CH_3$ | $CO_2(CH_2)_2CH_3$ |
| O | H | F | $CH_3$ | 1 | 6-$CH_3$ | $CO_2(CH_2)_2CH_3$ |
| S | F | F | $CH_3$ | 1 | 6-$CH_3$ | $CO_2(CH_2)_2CH_3$ |
| O | F | F | $CH_3$ | 1 | 6-$CH_3$ | $CO_2(CH_2)_2CH_3$ |
| S | H | Cl | $CH_3$ | 1 | 6-$CH_3$ | $CO_2(CH_2)_2CH_3$ |
| O | H | Cl | $CH_3$ | 1 | 6-$CH_3$ | $CO_2(CH_2)_2CH_3$ |
| S | F | Cl | $CH_3$ | 1 | 6-$CH_3$ | $CO_2(CH_2)_2CH_3$ |
| O | F | Cl | $CH_3$ | 1 | 6-$CH_3$ | $CO_2(CH_2)_2CH_3$ |
| S | H | F | H | 1 | 6-$CH_3$ | $CO_2CH(CH_3)_2$ |
| O | H | F | H | 1 | 6-$CH_3$ | $CO_2CH(CH_3)_2$ |
| S | F | F | H | 1 | 6-$CH_3$ | $CO_2CH(CH_3)_2$ |
| O | F | F | H | 1 | 6-$CH_3$ | $CO_2CH(CH_3)_2$ |
| S | H | Cl | H | 1 | 6-$CH_3$ | $CO_2CH(CH_3)_2$ |
| O | H | Cl | H | 1 | 6-$CH_3$ | $CO_2CH(CH_3)_2$ |
| S | F | Cl | H | 1 | 6-$CH_3$ | $CO_2CH(CH_3)_2$ |
| O | F | Cl | H | 1 | 6-$CH_3$ | $CO_2CH(CH_3)_2$ |
| S | H | F | $CH_3$ | 1 | 6-$CH_3$ | $CO_2CH(CH_3)_2$ |
| O | H | F | $CH_3$ | 1 | 6-$CH_3$ | $CO_2CH(CH_3)_2$ |
| S | F | F | $CH_3$ | 1 | 6-$CH_3$ | $CO_2CH(CH_3)_2$ |
| O | F | F | $CH_3$ | 1 | 6-$CH_3$ | $CO_2CH(CH_3)_2$ |
| S | H | Cl | $CH_3$ | 1 | 6-$CH_3$ | $CO_2CH(CH_3)_2$ |
| O | H | Cl | $CH_3$ | 1 | 6-$CH_3$ | $CO_2CH(CH_3)_2$ |
| S | F | Cl | $CH_3$ | 1 | 6-$CH_3$ | $CO_2CH(CH_3)_2$ |
| O | F | Cl | $CH_3$ | 1 | 6-$CH_3$ | $CO_2CH(CH_3)_2$ |
| S | H | F | H | 1 | 6-$CH_3$ | $CO_2(CH_2)_3CH_3$ |
| O | H | F | H | 1 | 6-$CH_3$ | $CO_2(CH_2)_3CH_3$ |
| S | F | F | H | 1 | 6-$CH_3$ | $CO_2(CH_2)_3CH_3$ |
| O | F | F | H | 1 | 6-$CH_3$ | $CO_2(CH_2)_3CH_3$ |
| S | H | Cl | H | 1 | 6-$CH_3$ | $CO_2(CH_2)_3CH_3$ |
| O | H | Cl | H | 1 | 6-$CH_3$ | $CO_2(CH_2)_3CH_3$ |
| S | F | Cl | H | 1 | 6-$CH_3$ | $CO_2(CH_2)_3CH_3$ |
| O | F | Cl | H | 1 | 6-$CH_3$ | $CO_2(CH_2)_3CH_3$ |
| S | H | F | $CH_3$ | 1 | 6-$CH_3$ | $CO_2(CH_2)_3CH_3$ |
| O | H | F | $CH_3$ | 1 | 6-$CH_3$ | $CO_2(CH_2)_3CH_3$ |
| S | F | F | $CH_3$ | 1 | 6-$CH_3$ | $CO_2(CH_2)_3CH_3$ |
| O | F | F | $CH_3$ | 1 | 6-$CH_3$ | $CO_2(CH_2)_3CH_3$ |
| S | H | Cl | $CH_3$ | 1 | 6-$CH_3$ | $CO_2(CH_2)_3CH_3$ |
| O | H | Cl | $CH_3$ | 1 | 6-$CH_3$ | $CO_2(CH_2)_3CH_3$ |
| S | F | Cl | $CH_3$ | 1 | 6-$CH_3$ | $CO_2(CH_2)_3CH_3$ |
| O | F | Cl | $CH_3$ | 1 | 6-$CH_3$ | $CO_2(CH_2)_3CH_3$ |
| S | H | F | H | 1 | 6-$CH_3$ | $CO_2(CH_2)_2OCH_3$ |
| O | H | F | H | 1 | 6-$CH_3$ | $CO_2(CH_2)_2OCH_3$ |
| S | F | F | H | 1 | 6-$CH_3$ | $CO_2(CH_2)_2OCH_3$ |
| O | F | F | H | 1 | 6-$CH_3$ | $CO_2(CH_2)_2OCH_3$ |
| S | H | Cl | H | 1 | 6-$CH_3$ | $CO_2(CH_2)_2OCH_3$ |
| O | H | Cl | H | 1 | 6-$CH_3$ | $CO_2(CH_2)_2OCH_3$ |
| S | F | Cl | H | 1 | 6-$CH_3$ | $CO_2(CH_2)_2OCH_3$ |
| O | F | Cl | H | 1 | 6-$CH_3$ | $CO_2(CH_2)_2OCH_3$ |

TABLE 1-continued

| X | R¹ | R² | R³ | m | R⁵ | R⁴ |
|---|----|----|----|---|----|----|
| S | H | F | CH₃ | 1 | 6-CH₃ | CO₂(CH₂)₂OCH₃ |
| O | H | F | CH₃ | 1 | 6-CH₃ | CO₂(CH₂)₂OCH₃ |
| S | F | F | CH₃ | 1 | 6-CH₃ | CO₂(CH₂)₂OCH₃ |
| O | F | F | CH₃ | 1 | 6-CH₃ | CO₂(CH₂)₂OCH₃ |
| S | H | Cl | CH₃ | 1 | 6-CH₃ | CO₂(CH₂)₂OCH₃ |
| O | H | Cl | CH₃ | 1 | 6-CH₃ | CO₂(CH₂)₂OCH₃ |
| S | F | Cl | CH₃ | 1 | 6-CH₃ | CO₂(CH₂)₂OCH₃ |
| O | F | Cl | CH₃ | 1 | 6-CH₃ | CO₂(CH₂)₂OCH₃ |
| S | H | F | H | 1 | 6-CH₃ | CO₂(CH₂)₂OCH₂CH₃ |
| O | H | F | H | 1 | 6-CH₃ | CO₂(CH₂)₂OCH₂CH₃ |
| S | F | F | H | 1 | 6-CH₃ | CO₂(CH₂)₂OCH₂CH₃ |
| O | F | F | H | 1 | 6-CH₃ | CO₂(CH₂)₂OCH₂CH₃ |
| S | H | Cl | H | 1 | 6-CH₃ | CO₂(CH₂)₂OCH₂CH₃ |
| O | H | Cl | H | 1 | 6-CH₃ | CO₂(CH₂)₂OCH₂CH₃ |
| S | F | Cl | H | 1 | 6-CH₃ | CO₂(CH₂)₂OCH₂CH₃ |
| O | F | Cl | H | 1 | 6-CH₃ | CO₂(CH₂)₂OCH₂CH₃ |
| S | H | F | CH₃ | 1 | 6-CH₃ | CO₂(CH₂)₂OCH₂CH₃ |
| O | H | F | CH₃ | 1 | 6-CH₃ | CO₂(CH₂)₂OCH₂CH₃ |
| S | F | F | CH₃ | 1 | 6-CH₃ | CO₂(CH₂)₂OCH₂CH₃ |
| O | F | F | CH₃ | 1 | 6-CH₃ | CO₂(CH₂)₂OCH₂CH₃ |
| S | H | Cl | CH₃ | 1 | 6-CH₃ | CO₂(CH₂)₂OCH₂CH₃ |
| O | H | Cl | CH₃ | 1 | 6-CH₃ | CO₂(CH₂)₂OCH₂CH₃ |
| S | F | Cl | CH₃ | 1 | 6-CH₃ | CO₂(CH₂)₂OCH₂CH₃ |
| O | F | Cl | CH₃ | 1 | 6-CH₃ | CO₂(CH₂)₂OCH₂CH₃ |
| S | H | F | H | 1 | 4,6-Di-CH₃ | CO₂CH₃ |
| O | H | F | H | 1 | 4,6-Di-CH₃ | CO₂CH₃ |
| S | F | F | H | 1 | 4,6-Di-CH₃ | CO₂CH₃ |
| O | F | F | H | 1 | 4,6-Di-CH₃ | CO₂CH₃ |
| S | H | Cl | H | 1 | 4,6-Di-CH₃ | CO₂CH₃ |
| O | H | Cl | H | 1 | 4,6-Di-CH₃ | CO₂CH₃ |
| S | F | Cl | H | 1 | 4,6-Di-CH₃ | CO₂CH₃ |
| O | F | Cl | H | 1 | 4,6-Di-CH₃ | CO₂CH₃ |
| S | H | F | CH₃ | 1 | 4,6-Di-CH₃ | CO₂CH₃ |
| O | H | F | CH₃ | 1 | 4,6-Di-CH₃ | CO₂CH₃ |
| S | F | F | CH₃ | 1 | 4,6-Di-CH₃ | CO₂CH₃ |
| O | F | F | CH₃ | 1 | 4,6-Di-CH₃ | CO₂CH₃ |
| S | H | Cl | CH₃ | 1 | 4,6-Di-CH₃ | CO₂CH₃ |
| O | H | Cl | CH₃ | 1 | 4,6-Di-CH₃ | CO₂CH₃ |
| S | F | Cl | CH₃ | 1 | 4,6-Di-CH₃ | CO₂CH₃ |
| O | F | Cl | CH₃ | 1 | 4,6-Di-CH₃ | CO₂CH₃ |
| S | H | F | H | 1 | 4,6-Di-CH₃ | CO₂CH₂CH₃ |
| O | H | F | H | 1 | 4,6-Di-CH₃ | CO₂CH₂CH₃ |
| S | F | F | H | 1 | 4,6-Di-CH₃ | CO₂CH₂CH₃ |
| O | F | F | H | 1 | 4,6-Di-CH₃ | CO₂CH₂CH₃ |
| S | H | Cl | H | 1 | 4,6-Di-CH₃ | CO₂CH₂CH₃ |
| O | H | Cl | H | 1 | 4,6-Di-CH₃ | CO₂CH₂CH₃ |
| S | F | Cl | H | 1 | 4,6-Di-CH₃ | CO₂CH₂CH₃ |
| O | F | Cl | H | 1 | 4,6-Di-CH₃ | CO₂CH₂CH₃ |
| S | H | F | CH₃ | 1 | 4,6-Di-CH₃ | CO₂CH₂CH₃ |
| O | H | F | CH₃ | 1 | 4,6-Di-CH₃ | CO₂CH₂CH₃ |
| S | F | F | CH₃ | 1 | 4,6-Di-CH₃ | CO₂CH₂CH₃ |
| O | F | F | CH₃ | 1 | 4,6-Di-CH₃ | CO₂CH₂CH₃ |
| S | H | Cl | CH₃ | 1 | 4,6-Di-CH₃ | CO₂CH₂CH₃ |
| O | H | Cl | CH₃ | 1 | 4,6-Di-CH₃ | CO₂CH₂CH₃ |
| S | F | Cl | CH₃ | 1 | 4,6-Di-CH₃ | CO₂CH₂CH₃ |
| O | F | Cl | CH₃ | 1 | 4,6-Di-CH₃ | CO₂CH₂CH₃ |
| S | H | F | H | 1 | 4,6-Di-CH₃ | CO₂(CH₂)₂CH₃ |
| O | H | F | H | 1 | 4,6-Di-CH₃ | CO₂(CH₂)₂CH₃ |
| S | F | F | H | 1 | 4,6-Di-CH₃ | CO₂(CH₂)₂CH₃ |
| O | F | F | H | 1 | 4,6-Di-CH₃ | CO₂(CH₂)₂CH₃ |
| S | H | Cl | H | 1 | 4,6-Di-CH₃ | CO₂(CH₂)₂CH₃ |
| O | H | Cl | H | 1 | 4,6-Di-CH₃ | CO₂(CH₂)₂CH₃ |
| S | F | Cl | H | 1 | 4,6-Di-CH₃ | CO₂(CH₂)₂CH₃ |
| O | F | Cl | H | 1 | 4,6-Di-CH₃ | CO₂(CH₂)₂CH₃ |
| S | H | F | CH₃ | 1 | 4,6-Di-CH₃ | CO₂(CH₂)₂CH₃ |
| O | H | F | CH₃ | 1 | 4,6-Di-CH₃ | CO₂(CH₂)₂CH₃ |
| S | F | F | CH₃ | 1 | 4,6-Di-CH₃ | CO₂(CH₂)₂CH₃ |
| O | F | F | CH₃ | 1 | 4,6-Di-CH₃ | CO₂(CH₂)₂CH₃ |
| S | H | Cl | CH₃ | 1 | 4,6-Di-CH₃ | CO₂(CH₂)₂CH₃ |
| O | H | Cl | CH₃ | 1 | 4,6-Di-CH₃ | CO₂(CH₂)₂CH₃ |
| S | F | Cl | CH₃ | 1 | 4,6-Di-CH₃ | CO₂(CH₂)₂CH₃ |
| O | F | Cl | CH₃ | 1 | 4,6-Di-CH₃ | CO₂(CH₂)₂CH₃ |
| S | H | F | H | 1 | 4,6-Di-CH₃ | CO₂CH(CH₃)₂ |
| O | H | F | H | 1 | 4,6-Di-CH₃ | CO₂CH(CH₃)₂ |
| S | F | F | H | 1 | 4,6-Di-CH₃ | CO₂CH(CH₃)₂ |
| O | F | F | H | 1 | 4,6-Di-CH₃ | CO₂CH(CH₃)₂ |
| S | H | Cl | H | 1 | 4,6-Di-CH₃ | CO₂CH(CH₃)₂ |
| O | H | Cl | H | 1 | 4,6-Di-CH₃ | CO₂CH(CH₃)₂ |
| S | F | Cl | H | 1 | 4,6-Di-CH₃ | CO₂CH(CH₃)₂ |
| O | F | Cl | H | 1 | 4,6-Di-CH₃ | CO₂CH(CH₃)₂ |
| S | H | F | CH₃ | 1 | 4,6-Di-CH₃ | CO₂CH(CH₃)₂ |

TABLE 1-continued

| X | R¹ | R² | R³ | m | R⁵ | R⁴ |
|---|----|----|-----|---|----|-----|
| O | H | F | CH₃ | 1 | 4,6-Di-CH₃ | CO₂CH(CH₃)₂ |
| S | F | F | CH₃ | 1 | 4,6-Di-CH₃ | CO₂CH(CH₃)₂ |
| O | F | F | CH₃ | 1 | 4,6-Di-CH₃ | CO₂CH(CH₃)₂ |
| S | H | Cl | CH₃ | 1 | 4,6-Di-CH₃ | CO₂CH(CH₃)₂ |
| O | H | Cl | CH₃ | 1 | 4,6-Di-CH₃ | CO₂CH(CH₃)₂ |
| S | F | Cl | CH₃ | 1 | 4,6-Di-CH₃ | CO₂CH(CH₃)₂ |
| O | F | Cl | CH₃ | 1 | 4,6-Di-CH₃ | CO₂CH(CH₃)₂ |
| S | H | F | H | 1 | 4,6-Di-CH₃ | CO₂(CH₂)₃CH₃ |
| O | H | F | H | 1 | 4,6-Di-CH₃ | CO₂(CH₂)₃CH₃ |
| S | F | F | H | 1 | 4,6-Di-CH₃ | CO₂(CH₂)₃CH₃ |
| O | F | F | H | 1 | 4,6-Di-CH₃ | CO₂(CH₂)₃CH₃ |
| S | H | Cl | H | 1 | 4,6-Di-CH₃ | CO₂(CH₂)₃CH₃ |
| O | H | Cl | H | 1 | 4,6-Di-CH₃ | CO₂(CH₂)₃CH₃ |
| S | F | Cl | H | 1 | 4,6-Di-CH₃ | CO₂(CH₂)₃CH₃ |
| O | F | Cl | H | 1 | 4,6-Di-CH₃ | CO₂(CH₂)₃CH₃ |
| S | H | F | CH₃ | 1 | 4,6-Di-CH₃ | CO₂(CH₂)₃CH₃ |
| O | H | F | CH₃ | 1 | 4,6-Di-CH₃ | CO₂(CH₂)₃CH₃ |
| S | F | F | CH₃ | 1 | 4,6-Di-CH₃ | CO₂(CH₂)₃CH₃ |
| O | F | F | CH₃ | 1 | 4,6-Di-CH₃ | CO₂(CH₂)₃CH₃ |
| S | H | Cl | CH₃ | 1 | 4,6-Di-CH₃ | CO₂(CH₂)₃CH₃ |
| O | H | Cl | CH₃ | 1 | 4,6-Di-CH₃ | CO₂(CH₂)₃CH₃ |
| S | F | Cl | CH₃ | 1 | 4,6-Di-CH₃ | CO₂(CH₂)₃CH₃ |
| O | F | Cl | CH₃ | 1 | 4,6-Di-CH₃ | CO₂(CH₂)₃CH₃ |
| S | H | F | H | 1 | 4,6-Di-CH₃ | CO₂(CH₂)₂OCH₃ |
| O | H | F | H | 1 | 4,6-Di-CH₃ | CO₂(CH₂)₂OCH₃ |
| S | F | F | H | 1 | 4,6-Di-CH₃ | CO₂(CH₂)₂OCH₃ |
| O | F | F | H | 1 | 4,6-Di-CH₃ | CO₂(CH₂)₂OCH₃ |
| S | H | Cl | H | 1 | 4,6-Di-CH₃ | CO₂(CH₂)₂OCH₃ |
| O | H | Cl | H | 1 | 4,6-Di-CH₃ | CO₂(CH₂)₂OCH₃ |
| S | F | Cl | H | 1 | 4,6-Di-CH₃ | CO₂(CH₂)₂OCH₃ |
| O | F | Cl | H | 1 | 4,6-Di-CH₃ | CO₂(CH₂)₂OCH₃ |
| S | H | F | CH₃ | 1 | 4,6-Di-CH₃ | CO₂(CH₂)₂OCH₃ |
| O | H | F | CH₃ | 1 | 4,6-Di-CH₃ | CO₂(CH₂)₂OCH₃ |
| S | F | F | CH₃ | 1 | 4,6-Di-CH₃ | CO₂(CH₂)₂OCH₃ |
| O | F | F | CH₃ | 1 | 4,6-Di-CH₃ | CO₂(CH₂)₂OCH₃ |
| S | H | Cl | CH₃ | 1 | 4,6-Di-CH₃ | CO₂(CH₂)₂OCH₃ |
| O | H | Cl | CH₃ | 1 | 4,6-Di-CH₃ | CO₂(CH₂)₂OCH₃ |
| S | F | Cl | CH₃ | 1 | 4,6-Di-CH₃ | CO₂(CH₂)₂OCH₃ |
| O | F | Cl | CH₃ | 1 | 4,6-Di-CH₃ | CO₂(CH₂)₂OCH₃ |
| S | H | F | H | 1 | 4,6-Di-CH₃ | CO₂(CH₂)₂OCH₂CH₃ |
| O | H | F | H | 1 | 4,6-Di-CH₃ | CO₂(CH₂)₂OCH₂CH₃ |
| S | F | F | H | 1 | 4,6-Di-CH₃ | CO₂(CH₂)₂OCH₂CH₃ |
| O | F | F | H | 1 | 6-CH₃ | CO₂(CH₂)₂OCH₂CH₃ |
| S | H | Cl | H | 1 | 6-CH₃ | CO₂(CH₂)₂OCH₂CH₃ |
| O | H | Cl | H | 1 | 6-CH₃ | CO₂(CH₂)₂OCH₂CH₃ |
| S | F | Cl | H | 1 | 6-CH₃ | CO₂(CH₂)₂OCH₂CH₃ |
| O | F | Cl | H | 1 | 6-CH₃ | CO₂(CH₂)₂OCH₂CH₃ |
| S | H | F | CH₃ | 1 | 6-CH₃ | CO₂(CH₂)₂OCH₂CH₃ |
| O | H | F | CH₃ | 1 | 6-CH₃ | CO₂(CH₂)₂OCH₂CH₃ |
| S | F | F | CH₃ | 1 | 6-CH₃ | CO₂(CH₂)₂OCH₂CH₃ |
| O | F | F | CH₃ | 1 | 6-CH₃ | CO₂(CH₂)₂OCH₂CH₃ |
| S | H | Cl | CH₃ | 1 | 6-CH₃ | CO₂(CH₂)₂OCH₂CH₃ |
| O | H | Cl | CH₃ | 1 | 6-CH₃ | CO₂(CH₂)₂OCH₂CH₃ |
| S | F | Cl | CH₃ | 1 | 6-CH₃ | CO₂(CH₂)₂OCH₂CH₃ |
| O | F | Cl | CH₃ | 1 | 6-CH₃ | CO₂(CH₂)₂OCH₂CH₃ |
| S | H | F | H | 0 | H | H |
| O | H | F | H | 0 | H | H |
| S | F | F | H | 0 | H | H |
| O | F | F | H | 0 | H | H |
| S | H | Cl | H | 0 | H | H |
| O | H | Cl | H | 0 | H | H |
| S | F | Cl | H | 0 | H | H |
| O | F | Cl | H | 0 | H | H |
| S | H | F | CH₃ | 0 | H | H |
| O | H | F | CH₃ | 0 | H | H |
| S | F | F | CH₃ | 0 | H | H |
| O | F | F | CH₃ | 0 | H | H |
| S | H | Cl | CH₃ | 0 | H | H |
| O | H | Cl | CH₃ | 0 | H | H |
| S | F | Cl | CH₃ | 0 | H | H |
| O | F | Cl | CH₃ | 0 | H | H |
| S | H | F | H | 0 | 4-CH₃ | H |
| O | H | F | H | 0 | 4-CH₃ | H |
| S | F | F | H | 0 | 4-CH₃ | H |
| O | F | F | H | 0 | 4-CH₃ | H |
| S | H | Cl | H | 0 | 4-CH₃ | H |
| O | H | Cl | H | 0 | 4-CH₃ | H |
| S | F | Cl | H | 0 | 4-CH₃ | H |
| O | F | Cl | H | 0 | 4-CH₃ | H |
| S | H | F | CH₃ | 0 | 4-CH₃ | H |
| O | H | F | CH₃ | 0 | 4-CH₃ | H |

TABLE 1-continued

| X | R¹ | R² | R³ | m | R⁵ | R⁴ |
|---|----|----|----|---|----|----|
| S | F | F | CH₃ | 0 | 4-CH₃ | H |
| O | F | F | CH₃ | 0 | 4-CH₃ | H |
| S | H | Cl | CH₃ | 0 | 4-CH₃ | H |
| O | H | Cl | CH₃ | 0 | 4-CH₃ | H |
| S | F | Cl | CH₃ | 0 | 4-CH₃ | H |
| O | F | Cl | CH₃ | 0 | 4-CH₃ | H |
| S | H | F | H | 0 | 4,5-Di-CH₃ | H |
| O | H | F | H | 0 | 4,5-Di-CH₃ | H |
| S | F | F | H | 0 | 4,5-Di-CH₃ | H |
| O | F | F | H | 0 | 4,5-Di-CH₃ | H |
| S | H | Cl | H | 0 | 4,5-Di-CH₃ | H |
| O | H | Cl | H | 0 | 4,5-Di-CH₃ | H |
| S | F | Cl | H | 0 | 4,5-Di-CH₃ | H |
| O | F | Cl | H | 0 | 4,5-Di-CH₃ | H |
| S | H | F | CH₃ | 0 | 4,5-Di-CH₃ | H |
| O | H | F | CH₃ | 0 | 4,5-Di-CH₃ | H |
| S | F | F | CH₃ | 0 | 4,5-Di-CH₃ | H |
| O | F | F | CH₃ | 0 | 4,5-Di-CH₃ | H |
| S | H | Cl | CH₃ | 0 | 4,5-Di-CH₃ | H |
| O | H | Cl | CH₃ | 0 | 4,5-Di-CH₃ | H |
| S | F | Cl | CH₃ | 0 | 4,5-Di-CH₃ | H |
| O | F | Cl | CH₃ | 0 | 4,5-Di-CH₃ | H |
| S | H | F | H | 0 | 4-CH₂CH₃ | H |
| O | H | F | H | 0 | 4-CH₂CH₃ | H |
| S | F | F | H | 0 | 4-CH₂CH₃ | H |
| O | F | F | H | 0 | 4-CH₂CH₃ | H |
| S | H | Cl | H | 0 | 4-CH₂CH₃ | H |
| O | H | Cl | H | 0 | 4-CH₂CH₃ | H |
| S | F | Cl | H | 0 | 4-CH₂CH₃ | H |
| O | F | Cl | H | 0 | 4-CH₂CH₃ | H |
| S | H | F | CH₃ | 0 | 4-CH₂CH₃ | H |
| O | H | F | CH₃ | 0 | 4-CH₂CH₃ | H |
| S | F | F | CH₃ | 0 | 4-CH₂CH₃ | H |
| O | F | F | CH₃ | 0 | 4-CH₂CH₃ | H |
| S | H | Cl | CH₃ | 0 | 4-CH₂CH₃ | H |
| O | H | Cl | CH₃ | 0 | 4-CH₂CH₃ | H |
| S | F | Cl | CH₃ | 0 | 4-CH₂CH₃ | H |
| O | F | Cl | CH₃ | 0 | 4-CH₂CH₃ | H |
| S | H | F | H | 1 | H | H |
| O | H | F | H | 1 | H | H |
| S | F | F | H | 1 | H | H |
| O | F | F | H | 1 | H | H |
| S | H | Cl | H | 1 | H | H |
| O | H | Cl | H | 1 | H | H |
| S | F | Cl | H | 1 | H | H |
| O | F | Cl | H | 1 | H | H |
| S | H | F | CH₃ | 1 | H | H |
| O | H | F | CH₃ | 1 | H | H |
| S | F | F | CH₃ | 1 | H | H |
| O | F | F | CH₃ | 1 | H | H |
| S | H | Cl | CH₃ | 1 | H | H |
| O | H | Cl | CH₃ | 1 | H | H |
| S | F | Cl | CH₃ | 1 | H | H |
| O | F | Cl | CH₃ | 1 | H | H |
| S | H | F | H | 1 | 4-CH₃ | H |
| O | H | F | H | 1 | 4-CH₃ | H |
| S | F | F | H | 1 | 4-CH₃ | H |
| O | F | F | H | 1 | 4-CH₃ | H |
| S | H | Cl | H | 1 | 4-CH₃ | H |
| O | H | Cl | H | 1 | 4-CH₃ | H |
| S | F | Cl | H | 1 | 4-CH₃ | H |
| O | F | Cl | H | 1 | 4-CH₃ | H |
| S | H | F | CH₃ | 1 | 4-CH₃ | H |
| O | H | F | CH₃ | 1 | 4-CH₃ | H |
| S | F | F | CH₃ | 1 | 4-CH₃ | H |
| O | F | F | CH₃ | 1 | 4-CH₃ | H |
| S | H | Cl | CH₃ | 1 | 4-CH₃ | H |
| O | H | Cl | CH₃ | 1 | 4-CH₃ | H |
| S | F | Cl | CH₃ | 1 | 4-CH₃ | H |
| O | F | Cl | CH₃ | 1 | 4-CH₃ | H |
| S | H | F | H | 1 | 4,6-Di-CH₃ | H |
| O | H | F | H | 1 | 4,6-Di-CH₃ | H |
| S | F | F | H | 1 | 4,6-Di-CH₃ | H |
| O | F | F | H | 1 | 4,6-Di-CH₃ | H |
| S | H | Cl | H | 1 | 4,6-Di-CH₃ | H |
| O | H | Cl | H | 1 | 4,6-Di-CH₃ | H |
| S | F | Cl | H | 1 | 4,6-Di-CH₃ | H |
| O | F | Cl | H | 1 | 4,6-Di-CH₃ | H |
| S | H | F | CH₃ | 1 | 4,6-Di-CH₃ | H |
| O | H | F | CH₃ | 1 | 4,6-Di-CH₃ | H |
| S | F | F | CH₃ | 1 | 4,6-Di-CH₃ | H |

TABLE 1-continued

| X | R¹ | R² | R³ | m | R⁵ | R⁴ |
|---|----|----|----|----|----|----|
| O | F | F | CH₃ | 1 | 4,6-Di-CH₃ | H |
| S | H | Cl | CH₃ | 1 | 4,6-Di-CH₃ | H |
| O | H | Cl | CH₃ | 1 | 4,6-Di-CH₃ | H |
| S | F | Cl | CH₃ | 1 | 4,6-Di-CH₃ | H |
| O | F | Cl | CH₃ | 1 | 4,6-Di-CH₃ | H |
| S | H | F | H | 1 | 4-CH₂CH₃ | H |
| O | H | F | H | 1 | 4-CH₂CH₃ | H |
| S | F | F | H | 1 | 4-CH₂CH₃ | H |
| O | F | F | H | 1 | 4-CH₂CH₃ | H |
| S | H | Cl | H | 1 | 4-CH₂CH₃ | H |
| O | H | Cl | H | 1 | 4-CH₂CH₃ | H |
| S | F | Cl | H | 1 | 4-CH₂CH₃ | H |
| O | F | Cl | H | 1 | 4-CH₂CH₃ | H |
| S | H | F | CH₃ | 1 | 4-CH₂CH₃ | H |
| O | H | F | CH₃ | 1 | 4-CH₂CH₃ | H |
| S | F | F | CH₃ | 1 | 4-CH₂CH₃ | H |
| O | F | F | CH₃ | 1 | 4-CH₂CH₃ | H |
| S | H | Cl | CH₃ | 1 | 4-CH₂CH₃ | H |
| O | H | Cl | CH₃ | 1 | 4-CH₂CH₃ | H |
| S | F | Cl | CH₃ | 1 | 4-CH₂CH₃ | H |
| O | F | Cl | CH₃ | 1 | 4-CH₂CH₃ | H |

The thiadiazabicyclononane derivatives I. and herbicidal agents containing them, may be applied for instance in the form of directly separable solutions, powders, suspensions including high-percentage aqueous, oily or other suspensions), dispersions, emulsions, oil dispersions, pastes, dusts broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are generally suitable for the preparation of directly separable solutions, emulsions, pastes and oil dispersions. Examples of suitable inert additives are mineral oil fractions of medium to high boiling point, such as kerosene or diesel oil further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol cyclohexanol, cyclohexanone, chlorobenzene, isophorone etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent adherent, emulsifying or dispersing agent and possibly solvent or oil.

Examples of surfactants are: alkali metal, alkaline earth metal and ammonium salts of aromatic sulfonic acids, e.g., ligninsulfonic acid phenolsulfonic acid, naphthalenesulfonic acid and dibutylnaphthalenesulfonic acid and of fatty acids, alkyl and alkyl aryl sulfonates, and alkyl, lauryl ether and fatty alcohol sulfates, and salts of sulfated hexadecanols, heptadecanols and octadecanols salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol alkylphenol polyglycol ethers, tributylphenyl polyglycol ethers, alkylaryl polyether alcohols, isotridecyl alcohol, fatty alcohol ethylene oxide condensates ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids silica gels, silicates, talc, kaolin, attapulgus clay, limestone, lime, chalk, bole, loess, clay, dolomite, diatomaceous earth calcium sulfate, magnesium sulfate magnesium oxide ground plastics fertilizers such as ammonium sulfate, ammonium phosphate, ammonium nitrate and ureas, and vegetable products such as grain meals, bark meal, wood meal, and nutshell meal, cellulosic powders etc.

The formulations contain from 0.1 to 95, and preferably 0.5 to 90, % by weight of active ingredient. The active ingredients are used in a purity of 90 to 100 and preferably 95 to 100, % (according to the NMR spectrum).

Examples of formulations are as follows:

I. A solution of 90 parts by weight of compound no. 3.01 and 10 parts by weight of N-methyl-alpha-pyrrolidone, which is suitable for application in the form of very fine drops.

II. A mixture of 20 parts by weight of compound no. 3.02. 80 parts by weight of xylene 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely distributing the solution in water, a dispersion is obtained.

III. An aqueous dispersion of 20 parts by weight of compound no. 3.03. 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 3.04, 25 parts by weight of cyclohexanone, 65 parts by weight of a mineral oil fraction having a boiling point between 210 and 280° C., and 10 parts by weight of the adduct of 40 moles of ethylene oxide and 1 mole of castor oil.

V. A mixture triturated in a hammer mill of 20 parts by weight of compound no. 3.05, 3 parts by weight of the sodium salt of diisobutylnaphthalene-alpha-sulfonic acid, 17 parts by weight of a lignin-sulfonic acid obtained from a sulfite waste liquor, and 60 parts by weight of powdered silica gel; by uniformly distributing the mixture in 20,000 parts by weight of water, a spray liquor is obtained containing 0.1 % by weight of the active ingredient.

VI. An intimate mixture of 3 parts by weight of compound no. 3.07 and 97 parts by weight of particulate kaolin. This dust contains 3% by weight of the active ingredient.

VII. An intimate mixture consisting of 30 parts by weight of compound no. 3.11, 92 parts by weight of powdered silica gel and 8 parts by weight of paraffin oil which has been sprayed onto the surface of this silica gel. This formulation gives the active ingredient good adherence.

VIII. A stable oily dispersion of 20 parts by weight of compound no. 3.12, 2 parts of the calcium salt of dodecylbenzenesulfonic acid 8 parts of a fatty alcohol polyglycol ether, 2 parts of the sodium salt of a phenolsulfonic acid-urea-formaldehyde condensate and 68 parts of a paraffinic mineral oil.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched and the agents reach the soil or the unwanted plants growing beneath the crop plants (post-directed, lay-by treatment).

The application rates depend on the objective to be achieved, the time of the Year, the plants to be combated and their growth stage, and are from 0.001 to 3.0, preferably 0.01 to 1.0, kg of active ingredient per hectare.

In view of the numerous application methods possible, the compounds according to the invention, or agents containing them, may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes silvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn |

To increase the spectrum of action and to achieve synergistic effects, the acetals and thioacetals I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones uracils, benzofuran derivaties, cyclohexane-1,3-dione derivaties, quinolinecarboxylic acids (hetero)-aryloxyphenoxypropionic acid derivatives (salts, esters amides), etc.

It may also be useful to apply the herbicidal compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

EXAMPLE 1

9-[(4-Methyl-1,3-dithiolan-2-yl)-4-chlorophenylimino]-8-thia-1,6-diazabicyclo[4.3.0]nonan-7-one compound No. 3.12 in Table 3)

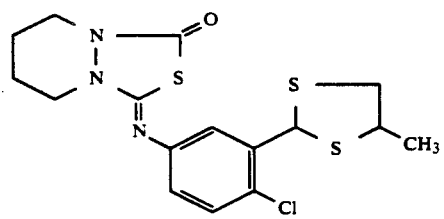

2.2 g (0.011 mol) of trichloromethyl chloroformate in 20 ml of methylene chloride were added dropwise at from 25 to 30° C. to a mixture of 3.7 g (0.01 mol) of N-[4-chloro-3-(3-methyl-1,3-dithiolan-2-yl)phenylthiocarbamoyl]hexahydropyridazine, 1.7 g (0.022 mol) of pyridine and 130 ml of methylene chloride. The mixture was then stirred at 25° C. for 2 hours, washed 3 times with 50 ml of water in each case until neutral and evaporated. The crude product was recrystallized from petroleum ether. Yield: 88%.

Precursor 1α)
4-Chloro-3-(4-methyl-1,3-dithiolan-2-yl)nitrobenzene

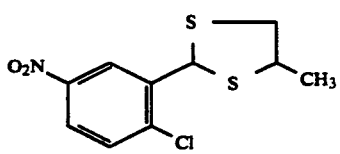

22.8 g (0.21 mol) of 1,2-propanedithiol were added to a solution of 37.1 g (0.2 mol) of 2-chloro-5-nitrobenzaldehyde, 1 g (5.10$^{-3}$ mol) of p-toluenesulfonic acid and 500 ml of toluene, and the mixture was refluxed for 5 hours on a water separator. After cooling, the solvent was removed and the residue was washed with petroleum ether. Yield: 94%; m.p.: 55° C.

Precursor 1β)
4-Chloro-3-(4-methyl-1,3-dithiolan-2-yl)aniline

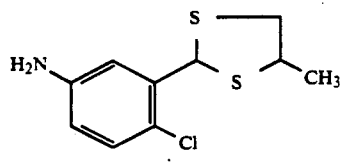

51.5 g (0.19 mol) of 4-chloro-3-(4-methyl-1,3-dithiolan-2-yl)nitrobenzene were added to a mixture of 31.5 g (0.56 mol) of iron powder in 100 ml of methanol and 150 ml of glacial acetic acid in a flask fitted with reflux condenser, and the mixture was heated for 2 hours. 400 ml of water were stirred into the mixture, the latter was filtered with suction, the filtrate was extracted with ethyl acetate, and the organic phase was washed with water, dried and evaporated. Yield: 81%; oil.

Precursor 1γ)
2-(4-Methyl-1,3-dithiolan-2-yl)-4-isothiocyanatochlorobenzene

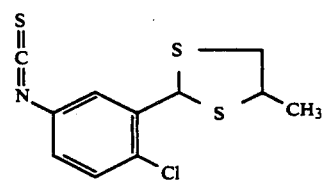

12.3 g (0.05 mol) of 4-chloro-3-(4-methyl)-1,3-dithiolan-2-yl)aniline in 100 ml of methylene chloride were added dropwise at from 25 to 30° C. to a mixture of 6.3 g (0.055 mol) of thiophosgene, 50 ml of methylene chloride and 100 ml of water. The mixture was stirred at 25° C. for 2 hours, and the organic phase was separated off, washed twice with 50 ml of saturated sodium bicarbonate solution and water in each case until neutral, dried and evaporated. Yield: 90%; oil.

Precursor 1δ)
N-[4-chloro-3-(3-methyl-1,3-dithiolan-2-yl)phenylthiocarbamoyl]hexahydropyridazine

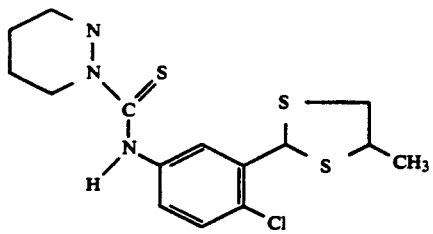

13 g (0.045 mol) of 2-(4-methyl-1,3-dithiolan-2-yl)-4-isothiocyanatochlorobenzene in 50 ml of tetrahydrofuran were added dropwise at from 25 to 30° C. to a solution of 4.3 g (0.05 mol) of piperazine in 200 ml of tetrahydrofuran. After 2 hours at 25° C., the solvent was removed. Yield: 59%; m.p.: 124–125° C.

EXAMPLE 2

7-[(1,3-Dithiolan-2-yl)-4-chlorophenylimino]-8-thia-1,6diazabicyclo[4.3.0]non-2-en -9-one (compound No. 3.04 in Table 3)

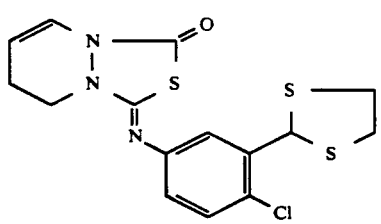

Two portions each of 1.2 g (11 mmol) of 1,3-propanedithiol were added to a mixture of 3.1 g (10 mmol) of 7-(2-formyl-4-chlorophenylimino)-8-thia-1,6-diazabicyclo[4.3.0]non-2-en-9-one, 0.1 g (0.5 mmol) of p-toluenesulfonic acid and 200 ml of toluene, and the mixture was refluxed for 15 hours while removing the water of reaction. The mixture was then washed twice with 50 ml of 10% strength by weight sodium hydroxide solution in each case and 3 times with water, and the product was subsequently worked up Yield: 63%.

Precursor 2α)

2-(1,3-Dioxolan-2-yl)-4-isothiocyanatochlorobenzene

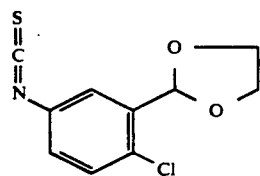

6.3 g (0.55 mol) of thiophosgene were added dropwise with ice cooling to a solution of 100 g (0.5 mol) of 4-chloro-3-(1,3-dioxolan-2-yl)aniline and 60 g (0.6 mol) of triethylamine in 1 l of dichloromethane. The mixture was stirred at 25° C. for 2 hours, washed 3 times with 500 ml of water in each case and then dried using sodium sulfate. The solvent was subsequently removed. Yield: quantitative; m.p.: 93–94° C.

Precursor 2β)

N-(4-chloro-3-(1,3-dioxolan-2-yl)phenylthiocarbamoyl]1,4,5,6-tetrahydropyridazine

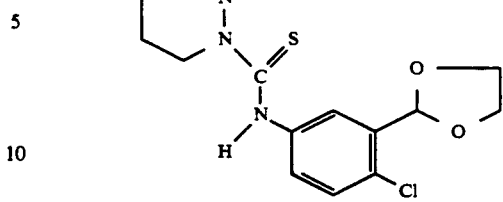

A solution of the crude precursor 2α) (about 0.5 mol of 2-(1,3-dioxolan-2-yl)-4-isothiocyanatochlorobenzene) in 500 ml of tetrahydrofuran was added dropwise at 25° C. to a solution of 42 g (0.5 mol) of 1,4,5,6-tetrahydropyridazine in 750 ml of tetrahydrofuran. The mixture was stirred at 25° C. for 2 hours, the solvent was removed, and the residue was stirred with 500 ml of ethanol. The solid material suspended in the solution was filtered off and dried. Yield: 58%; m.p.: 112–114° C.

Precursor 2γ)

2-Formyl-4-chlorophenylimino)-8-thia-1 6-diazabicyclo[4.3.0]non-2-en-9-one 50 g (0.25 mol) of trichloromethyl chloroformate in 200 ml of methylene chloride were added dropwise at from 25 to 30° C. to a mixture of 81.5 g (0.25 mol) of N[4-chloro-3-(1,3-dioxolan-2-yl) phenylthiocarbamoyl]-1,4,5,6-tetraydropyridazine, 43 g (0.55 mol) of pyridine and 500 ml of methylene chloride. The mixture was then stirred at 25° C. for 5 hours, and 500 ml of water were added dropwise with ice cooling. The phases were separated, and the organic phase was washed until neutral and evaporated. The residue was hydrolyzed for 20 hours at from 40 to 45° C. using 540 ml of concentrated acetic acid. 300 ml of water were then added to the solution at 25° C. The solid which formed was filtered off, washed with water until neutral and dried. Yield : 61%; m.p.: 145–146° C.

The physical data of the products I are shown in Table 3 below, in which further compounds I which were prepared or can be prepared in the same way are also shown.

TABLE 3

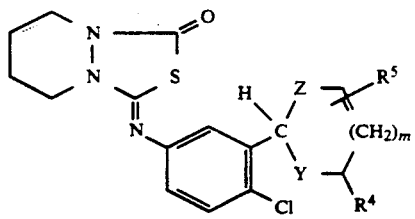

I (R$^1$, R$^3$ = H; R$^2$ = Cl; X = O)

| No. | Double bond in the thiadiazabicyclononane moiety | Y | Z | R$^4$ | R$^5$ | m | Phys. data mp [°C.]; IR [cm$^{-1}$]; NMR [ppm] |
|---|---|---|---|---|---|---|---|
| 3.01 | yes | S | S | H | H | 1 | 180–183 |
| 3.02 | yes | O | O | H | H | 0 | 1695, 1627, 1290, 1262 |
| 3.03 | yes | O | O | H | H | 1 | 129–130 |
| 3.04 | yes | S | S | H | H | 0 | 139–140 |
| 3.05 | yes | S | S | CH$_3$ | H | 0 | 1694, 1626, 1584, 1288, 1266 |
| 3.06 | yes | O | S | H | H | 0 | 1691, 1618, 1586, 1262 |
| 3.07 | yes | O | O | CH$_3$ | 6-CH$_3$ | 1 | 1694, 1630, 1592, 1263 |
| 3.08 | yes | O | O | CH$_3$ | 5-CH$_3$ | 0 | 1696, 1628, 1262, 1089 |
| 3.09 | yes | O | O | CH$_3$ | 5-CO—O(CH$_2$)$_3$CH$_3$ | 0 | 1731, 1697, 1628, 1266 |
| 3.10 | yes | O | O | CH$_3$ | 5-CO—O(CH$_2$)$_3$CH$_3$ | 0 | |
| 3.11 | yes | O | O | H | 5-CH$_2$OCH$_2$CH=CH$_2$ | 0 | 1696, 1627, 1263, 1093 |
| 3.12 | no | S | S | CH$_3$ | H | 0 | 121–122 |

Use examples

The herbicidal action of the thiadiazabicyclononane derivatives of the formula I is illustrated in the following greenhouse experiments.

The vessels employed were plastic flowerpots having a volume of 300 cm$^3$ and filled with a sandy loam containing about 3.0% humus. The seeds of the test plants were sown separately, according to species.

In the preemergence treatment, the active ingredients suspended or emulsified in water, were applied through finely distributing nozzles immediately after sowing. The vessels were lightly irrigated to induce germination and growth, and covered with transparent plastic hoods until the plants had taken root. This cover ensured uniform germination of the test plants, insofar as this was not impaired by the active ingredients.

For the postemergence treatment, the plants were grown depending on growth form to a height of 3 to 15 cm before being treated with the active ingredients, which were suspended or emulsified in water. The application rate for postemergence treatment was 0.03 kg/ha.

The pots were set up in the greenhouse, species from warmer climates in warmer areas (20 to 35° C.) and species from moderate climates at 10 to 25° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the experiments were Triticum aestivum cassia tora, Chenopodium album and Ipomoea spp.

The results show that compound no. 3.12, applied postemergence, completely destroyed the broadleaved plants, wheat, the crop plant, remained undamaged.

We claim:

1. Thiadiazabicyclononane derivatives of the general formula I

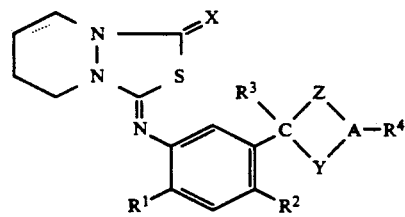

where the dotted bond is a possible additional bond and the substituents have the following meanings:

R$^1$ hydrogen or fluorine;
R$^2$ halogen;
R$^3$ hydrogen or C$_1$-C$_4$-alkyl;
R$^4$ hydrogen, C$_1$-C$_8$-alkoxycarbonyl, C$_3$-C$_6$-alkenyloxycarbonyl or C$_3$-C$_6$-alkynyloxycarbonyl, it being possible for each of these three groups to additionally bear a C$_1$-C$_4$-alkoxy radical;
X,Y,Z oxygen or sulfur;
A a C$_2$-C$_3$-alkylene chain which, in addition to R$^4$, may bear up to three, identical or different radicals R$^5$ hydroxyl, carboxyl C$_1$-C$_4$-alkyl or C$_1$-C$_6$-alkoxycarbonyl, and these last two radicals in turn may bear up to 5 halogen atoms and/or one of the following substituents: hydroxyl, cyano, mercapto, C$_1$-C$_4$-alkoxy, C$_1$-C$_6$-alkylthio, C$_3$-C$_6$-alkenyloxy, C$_3$-C$_6$-alkenylthio C$_3$-C$_6$-alkynyloxy, C$_3$-C$_6$-alkynylthio, C$_1$-C$_6$-alkylcarbonyloxy, C$_1$-C$_6$-alkoxycarbonyl, C$_1$-C$_6$-alkoxycarbonyl-C$_1$-C$_4$-alkoxy or C$_1$-C$_6$-alkoxycarbonyl-C$_1$-C$_6$-alkylthio.

2. Thiadiazabicyclononane derivatives I as set forth in claim 1 where R$^1$ and R$^3$ are hydrogen, R$^2$ is chlorine and x is oxygen.

3. Herbicidal agents containing a herbicidally effective amount of an acetal of the formula I as set forth in claim 1 and conventional additives.

4. Herbicidal agents as set forth in claim 3, containing a herbicidally effective amount of an acetal of the formula I and further active constituents.

5. A process for combating the growth of unwanted plants, wherein a herbicidally effective amount of an acetal of the formula I as set for in claim 1 is allowed to act on plants, their habitat or on seed.

* * * * *

UNITED STATES PATENT AND TRADEMARK OFFICE
CERTIFICATE OF CORRECTION

PATENT NO. : 5,106,408
DATED : April 21, 1992
INVENTOR(S) : Rueb, et al

It is certified that error appears in the above-indentified patent and that said Letters Patent is hereby corrected as shown below:

In Abstract

-in 3rd line after formula:

That part reading "$C_3-C_5$-alkyyloxycarbonyl" should read --$C_3-C_6$-alkynyloxycarbonyl--

-in 6th line after formula:

That part reading "a=$C_2-C_3$-alkylene chain" should read --A = $C_2-C_3$-alkylene chain--

UNITED STATES PATENT AND TRADEMARK OFFICE
CERTIFICATE OF CORRECTION

PATENT NO. : 5,106,408
DATED : April 21, 1992
INVENTOR(S) : RUEB, ET AL

It is certified that error appears in the above-indentified patent and that said Letters Patent is hereby corrected as shown below:

<u>In Claims</u>

<u>Claim 1, Col. 54, Line 52</u> please insert --,-- between "$C_3$-$C_6$-alkenylthio" and "$C_3$-$C_6$-alkinyloxy"

<u>Claim 5, Col. 54, Line 67</u>

That part reading "as set for in claim 1" should read --as set forth in claim 1--.

Signed and Sealed this

Third Day of August, 1993

Attest:

MICHAEL K. KIRK

Attesting Officer     Acting Commissioner of Patents and Trademarks